(12) United States Patent
Godfrey et al.

(10) Patent No.: US 12,410,083 B2
(45) Date of Patent: Sep. 9, 2025

(54) MICROBE-BASED SYSTEMS, COMPOSITIONS, AND METHODS THEREOF

(71) Applicant: University of Washington, Seattle, WA (US)

(72) Inventors: Bruce J. Godfrey, Seattle, WA (US); Mari-Karoliina Henriikka Winkler, Seattle, WA (US); David Stahl, Seattle, WA (US)

(73) Assignee: University of Washington, Seattle, WA (US)

( * ) Notice: Subject to any disclaimer, the term of this patent is extended or adjusted under 35 U.S.C. 154(b) by 472 days.

(21) Appl. No.: 17/791,676

(22) PCT Filed: Jan. 12, 2021

(86) PCT No.: PCT/US2021/013127
§ 371 (c)(1),
(2) Date: Jul. 8, 2022

(87) PCT Pub. No.: WO2021/146212
PCT Pub. Date: Jul. 22, 2021

(65) Prior Publication Data
US 2023/0046027 A1    Feb. 16, 2023

Related U.S. Application Data

(60) Provisional application No. 62/960,494, filed on Jan. 13, 2020.

(51) Int. Cl.
C02F 3/34 (2023.01)
C02F 3/10 (2023.01)
(Continued)

(52) U.S. Cl.
CPC ............. *C02F 3/348* (2013.01); *C02F 3/102* (2013.01); *C02F 3/307* (2013.01); *C02F 3/341* (2013.01);
(Continued)

(58) Field of Classification Search
CPC .......... C02F 3/348; C02F 3/102; C02F 3/307; C02F 3/341; C02F 3/302; C12M 25/10;
(Continued)

(56) References Cited

U.S. PATENT DOCUMENTS 5,580,770 A * 12/1996 DeFilippi ............... C02F 3/085
                                                       210/615
9,766,237 B2    9/2017 Jablonski
(Continued)

FOREIGN PATENT DOCUMENTS

JP       8-256773 A  * 10/1996
JP   2013121595 A  *  6/2013
(Continued)

OTHER PUBLICATIONS

Machine-generated English translation of KR 2006-0010801, generated on Nov. 22, 2024.*
(Continued)

*Primary Examiner* — Fred Prince
(74) *Attorney, Agent, or Firm* — CHRISTENSEN O'CONNOR JOHNSON KINDNESS PLLC

(57) ABSTRACT

The present disclosure describes a microorganism support structure, including a gas-permeable layer comprising two opposing surfaces; a microorganism adhesive coats at least one surface of the gas-permeable layer; and a microorganism disposed on the microorganism adhesive-coated surface of the layer. The microorganism adhesive enhances the
(Continued)

adhesion of the microorganism on the layer compared to a gas-permeable layer that does not have the microorganism adhesive.

20 Claims, 14 Drawing Sheets

Specification includes a Sequence Listing.

(51) Int. Cl.
  C02F 3/30    (2023.01)
  C12M 1/12    (2006.01)
  C12N 1/20    (2006.01)
  C12N 11/04   (2006.01)
(52) U.S. Cl.
  CPC ............... C12M 25/10 (2013.01); C12N 1/20 (2013.01); C12N 11/04 (2013.01); C02F 3/302 (2013.01); C12M 25/02 (2013.01); Y02W 10/10 (2015.05)
(58) Field of Classification Search
  CPC .......... C12M 25/02; C12N 1/20; C12N 11/04; Y02W 10/10
  USPC ........ 435/174, 176, 177, 180, 181; 210/615, 210/616, 617, 150, 151
  See application file for complete search history.

(56) References Cited

U.S. PATENT DOCUMENTS

| | | | |
|---|---|---|---|
| 2003/0104192 A1* | 6/2003 | Hester | C02F 3/108 |
| | | | 428/304.4 |
| 2007/0072187 A1 | 3/2007 | Blok | |
| 2011/0120949 A1 | 5/2011 | Watari | |
| 2012/0122219 A1 | 5/2012 | Lee | |
| 2012/0288912 A1* | 11/2012 | McCarthy | C12N 5/0075 |
| | | | 435/180 |
| 2015/0079597 A1 | 3/2015 | Flandrois | |
| 2017/0014543 A1 | 1/2017 | Xu | |
| 2019/0364856 A1 | 12/2019 | Minami | |
| 2019/0375662 A1 | 12/2019 | Novak | |
| 2020/0062627 A1* | 2/2020 | Cord-Ruwisch | C02F 3/302 |

FOREIGN PATENT DOCUMENTS

| | | | | |
|---|---|---|---|---|
| KR | 20060010801 A | * | 2/2006 | |
| WO | 9900151 A | | 1/1999 | |
| WO | 2005113456 A2 | | 12/2005 | |
| WO | WO-2008066244 A1 | * | 6/2008 | ............. C02F 3/108 |
| WO | 2017136561 A1 | | 8/2017 | |
| WO | 2019222333 | | 11/2019 | |

OTHER PUBLICATIONS

Machine-generated English translation of JP 2013-121595, generated on Mar. 27, 2025.*
Machine-generated English translation of JP 8-256773, generated on Mar. 27, 2025.*
International Preliminary Report on Patentability mailed Jul. 19, 2022, issued in the corresponding International Application No. PCT/US2021/013127, filed Jan. 12, 2021, 7 pages.
International Search Report and Written Opinion mailed Apr. 5, 2021, issued in the corresponding International Application No. PCT/US2021/013127, filed Jan. 12, 2021, 10 pages.
Annavajhala, Medini K., et al. "Comammox functionality identified in diverse engineered biological wastewater treatment systems." Environmental science & technology letters 5.2 (2018): 110-116.
Arrigo, Kevin R. "Marine microorganisms and global nutrient cycles." Nature 437.7057 (2005): 349-355.
Blackburne, Richard, et al. "Kinetic characterisation of an enriched Nitrospira culture with comparison to Nitrobacter." Water research 41.14 (2007): 3033-3042.
Bollmann, Annette, Elizabeth French, and Hendrikus J. Laanbroek. "Isolation, cultivation, and characterization of ammonia-oxidizing bacteria and archaea adapted to low ammonium concentrations." Methods in enzymology. vol. 486. Academic Press, 2011. 55-88.
Broda, E1. "Two kinds of lithotrophs missing in nature." Zeitschrift für allgemeine Mikrobiologie 17.6 (1977): 491-493.
Camejo, Pamela Y., et al. "Genome-enabled insights into the ecophysiology of the comammox bacterium "Candidatus Nitrospira nitrosa"." Msystems 2.5 (2017): e00059-17.
Cao, Yeshi, Mark van Loosdrecht, and Glen T. Daigger. "Mainstream partial nitritation-anammox in municipal wastewater treatment: status, bottlenecks, and further studies." Applied microbiology and biotechnology 101.4 (2017): 1365-1383.
Colville, Keegan, et al. "Effects of poly (L-lysine) substrates on attached *Escherichia coli* bacteria." Langmuir 26.4 (2010): 2639-2644.
Cotto, Irmarie, et al. "Long solids retention times and attached growth phase favor prevalence of comammox bacteria in nitrogen removal systems." Water research 169 (2020): 115268.
Daims, Holger, et al. "Complete nitrification by Nitrospira bacteria." Nature 528.7583 (2015): 504-509.
Devol, Allan H. "Solution to a marine mystery." Nature 422.6932 (2003): 575-576.
Edgar, Robert C. "Search and clustering orders of magnitude faster than BLAST." Bioinformatics 26.19 (2010): 2460-2461.
Edgar, Robert C. "Sintax: a simple non-Bayesian taxonomy classifier for 16S and ITS sequences." biorxiv (2016): 074161.
Edgar, Robert C. "UNOISE2: improved error-correction for Illumina 16S and ITS amplicon sequencing." BioRxiv (2016): 081257.
Füssel, Jessika, et al. "Nitrite oxidation in the Namibian oxygen minimum zone." The ISME journal 6.6 (2012): 1200-1209.
Gottshall, Ekaterina Y., et al. "Sustained nitrogen loss in a symbiotic association of Comammox Nitrospira and Anammox bacteria." Water Research 202 (2021): 117426.
Gruber, Nicolas, and James N. Galloway. "An Earth-system perspective of the global nitrogen cycle." Nature 451.7176 (2008): 293-296.
Hamersley, M. Robert, et al. "Anaerobic ammonium oxidation in the Peruvian oxygen minimum zone." Limnology and Oceanography 52.3 (2007): 923-933.
Kartal, Boran, Wim Geerts, and Mike SM Jetten. "Cultivation, detection, and ecophysiology of anaerobic ammonium-oxidizing bacteria." Methods in enzymology. vol. 486. Academic Press, 2011. 89-108.
Koch, Hanna, et al. "Expanded metabolic versatility of ubiquitous nitrite-oxidizing bacteria from the genus Nitrospira." Proceedings of the national academy of sciences 112.36 (2015): 11371-11376.
Konneke, Martin, et al. "Isolation of an autotrophic ammonia-oxidizing marine archaeon." Nature 437.22 (2005): 543-546.
Wang, Yao-Kuan, et al. "Comparison of Escherichia coli surface attachment methods for single-cell, in vivo microscopy." bioRxiv (2019): 648840.
Kuypers, Marcel MM, et al. "Anaerobic ammonium oxidation by anammox bacteria in the Black Sea." Nature 422.6932 (2003): 608-611.
Kuypers, Marcel MM, et al. "Massive nitrogen loss from the Benguela upwelling system through anaerobic ammonium oxidation." Proceedings of the National Academy of Sciences 102.18 (2005): 6478-6483.
Lam, Phyllis, et al. "Linking crenarchaeal and bacterial nitrification to anammox in the Black Sea." Proceedings of the National Academy of Sciences 104.17 (2007): 7104-7109.
Lam, Phyllis, et al. "Revising the nitrogen cycle in the Peruvian oxygen minimum zone." Proceedings of the National Academy of Sciences 106.12 (2009): 4752-4757.
Lawson, Christopher E., et al. "Metabolic network analysis reveals microbial community interactions in anammox granules." Nature communications 8.15416 (2017): 1-12.
Li, Meng, and Ji-Dong Gu. "Community structure and transcript responses of anammox bacteria, AOA, and AOB in mangrove

(56) References Cited

OTHER PUBLICATIONS sediment microcosms amended with ammonium and nitrite." Applied microbiology and biotechnology 97.22 (2013): 9859-9874.
Liu, Yiwen, et al. "Autotrophic nitrogen removal in membrane-aerated biofilms: Archaeal ammonia oxidation versus bacterial ammonia oxidation." Chemical Engineering Journal 302 (2016): 535-544.
Liu, Tao, et al. "High-level nitrogen removal by simultaneous partial nitritation, anammox and nitrite/nitrate-dependent anaerobic methane oxidation." Water Research 166 (2019): 115057.
Lonergan, N. E., L. D. Britt, and C. J. Sullivan. "Immobilizing live *Escherichia coli* for AFM studies of surface dynamics." Ultramicroscopy 137 (2014): 30-39.
Lotti, T., et al. "Simultaneous partial nitritation and anammox at low temperature with granular sludge." Water research 66 (2014): 111-121.
Lotti, T., et al. "The effect of nitrite inhibition on the anammox process." Water research 46.8 (2012): 2559-2569.
Louca, Stilianos, Michael Doebeli, and Laura Wegener Parfrey. "Correcting for 16S rRNA gene copy numbers in microbiome surveys remains an unsolved problem." Microbiome 6.41 (2018): 1-12.
Maidak, Bonnie L., et al. "The RDP (ribosomal database project)." Nucleic acids research 25.1 (1997): 109-110.
Marais, G. V. R., and G. A. Ekama. "The activated sludge process part I-steady state behaviour." Water Sa 2.4 (1976): 163-200.
Martens-Habbena, Willm, et al. "Ammonia oxidation kinetics determine niche separation of nitrifying Archaea and Bacteria." Nature 461.7266 (2009): 976-979.
Oshiki, Mamoru, et al. "Draft genome sequence of an anaerobic ammonium-oxidizing bacterium, "Candidatus Brocadia sinica"." Genome announcements 3.2 (2015): e00267-15.
Pan, Yuting, et al. "Modeling of the interaction among aerobic ammonium-oxidizing archaea/bacteria and anaerobic ammonium-oxidizing bacteria." Chemical Engineering Science 150 (2016): 35-40.
Pandey, C. B., et al. "DNRA: A short-circuit in biological N-cycling to conserve nitrogen in terrestrial ecosystems." Science of the Total Environment 738 (2020): 139710.
Parada, Alma E., David M. Needham, and Jed A. Fuhrman. "Every base matters: assessing small subunit rRNA primers for marine microbiomes with mock communities, time series and global field samples." Environmental microbiology 18.5 (2016): 1403-1414.
Park, Hee-Deung, and Daniel R. Noguera. "Nitrospira community composition in nitrifying reactors operated with two different dissolved oxygen levels." Journal of microbiology and biotechnology 18.8 (2008): 1470-1474.
Pitcher, Angela, et al. "Niche segregation of ammonia-oxidizing archaea and anammox bacteria in the Arabian Sea oxygen minimum zone." The ISME journal 5.12 (2011): 1896-1904.
Qin, Wei, et al. "Alternative strategies of nutrient acquisition and energy conservation map to the biogeography of marine ammonia-oxidizing archaea." The ISME journal 14.10 (2020): 2595-2609.
Quince, Christopher, et al. "Removing noise from pyrosequenced amplicons." BMC bioinformatics 12.38 (2011): 1-18.
Rittmann, Bruce E., and Perry L. McCarty. Environmental biotechnology: principles and applications. McGraw-Hill Education, 2001.
Russ, Lina, et al. "Genome analysis and heterologous expression of acetate-activating enzymes in the anammox bacterium Kuenenia stuttgartiensis." Archives of microbiology 194.11 (2012): 943-948.
Straka, Levi L., et al. "Affinity informs environmental cooperation between ammonia-oxidizing archaea (AOA) and anaerobic ammonia-oxidizing (Anammox) bacteria." The ISME journal 13.8 (2019): 1997-2004.
Strous, Marc, J. Gijs Kuenen, and Mike SM Jetten. "Key physiology of anaerobic ammonium oxidation." Applied and environmental microbiology 65.7 (1999): 3248-3250.
Sun, Xiaoyan, et al. "A novel and simple treatment for control of sulfide induced sewer concrete corrosion using free nitrous acid." Water Research 70 (2015): 279-287.
Sun, Xin, et al. "Uncultured Nitrospina-like species are major nitrite oxidizing bacteria in oxygen minimum zones." The ISME journal 13.10 (2019): 2391-2402.
Tchobanoglous, G.; Burton, F. L.; Stensel, H. D. Wastewater Engineering: Treatment and Resource Recovery, 4th ed.; McGraw Hill: New York, New York, 2014.
Terada, Akihiko, et al. "Redox-stratification controlled biofilm (ReSCoBi) for completely autotrophic nitrogen removal: The effect of co-versus counter-diffusion on reactor performance." Biotechnology and Bioengineering 97.1 (2007): 40-51.
Tourna, Maria, et al. "Nitrososphaera viennensis, an ammonia oxidizing archaeon from soil." Proceedings of the National Academy of Sciences 108.20 (2011): 8420-8425.
Tsushima, Ikuo, Tomonori Kindaichi, and Satoshi Okabe. "Quantification of anaerobic ammonium-oxidizing bacteria in enrichment cultures by real-time PCR." Water Research 41.4 (2007): 785-794.
Van de Graaf, Astrid A., et al. "Anaerobic oxidation of ammonium is a biologically mediated process." Applied and environmental microbiology 61.4 (1995): 1246-1251.
Van der Star, Wouter RL, et al. "Startup of reactors for anoxic ammonium oxidation: experiences from the first full-scale anammox reactor in Rotterdam." Water research 41.18 (2007): 4149-4163.
Van Teeseling, Muriel CF, et al. "Anammox Planctomycetes have a peptidoglycan cell wall." Nature communications 6.6878 (2015): 1-6.
Volcke, E. I. P., et al. "The granule size distribution in an anammox-based granular sludge reactor affects the conversion—Implications for modeling." Biotechnology and bioengineering 109.7 (2012): 1629-1636.
Voss, Maren, et al. "The marine nitrogen cycle: recent discoveries, uncertainties and the potential relevance of climate change." Philosophical Transactions of the Royal Society B: Biological Sciences 368.1621 (2013): 20130121.
Winkler, M. K., et al. "Factors influencing the density of aerobic granular sludge." Applied microbiology and biotechnology 97.16 (2013): 7459-7468.
Winkler, M-KH, R. Kleerebezem, and M. C. M. Van Loosdrecht. "Integration of anammox into the aerobic granular sludge process for main stream wastewater treatment at ambient temperatures." Water research 46.1 (2012): 136-144.
Winkler, Mari KH, and Levi Straka. "New directions in biological nitrogen removal and recovery from wastewater." Current opinion in biotechnology 57 (2019): 50-55.
Yan, Jia, et al. "Mimicking the oxygen minimum zones: stimulating interaction of aerobic archaeal and anaerobic bacterial ammonia oxidizers in a laboratory-scale model system." Environmental Microbiology 14.12 (2012): 3146-3158.
Yu, Xuejun, et al. "Synthesis of formate from CO2 gas catalyzed by an O2-tolerant NAD-dependent formate dehydrogenase and glucose dehydrogenase." Biochemistry 58.14 (2019): 1861-1868.
Tietgens, et al. "CO2, O2, and biomass monitoring in *Escherichia coli* shake flask culture: Following glucose-glycerin diauxie on-line," Nov. 17, 2017, entire document especially p. 2, Para 2.

\* cited by examiner

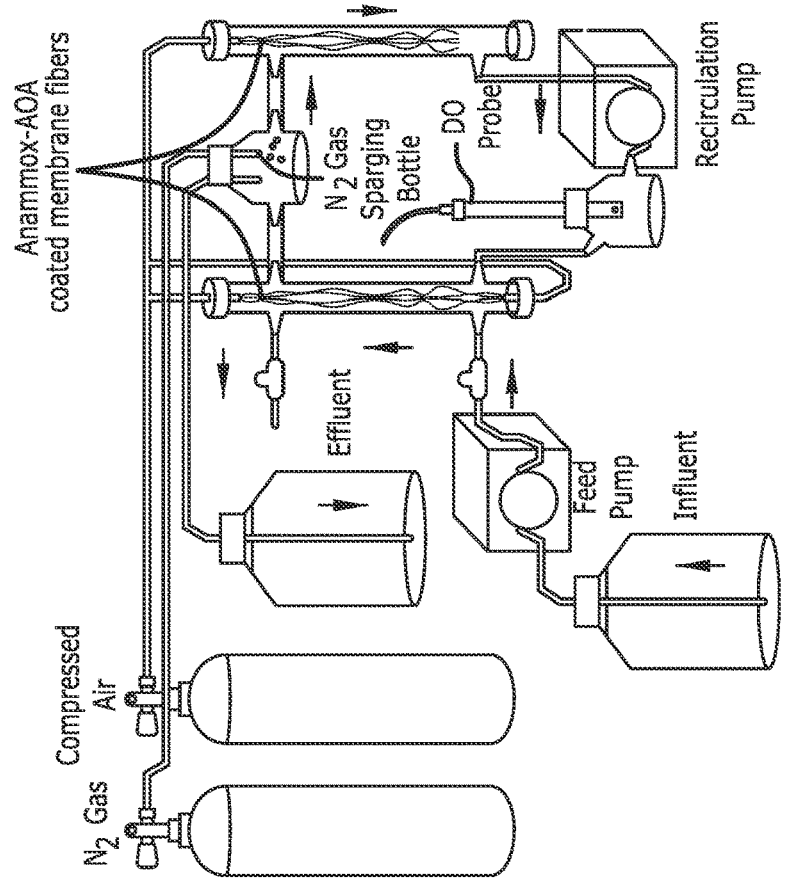
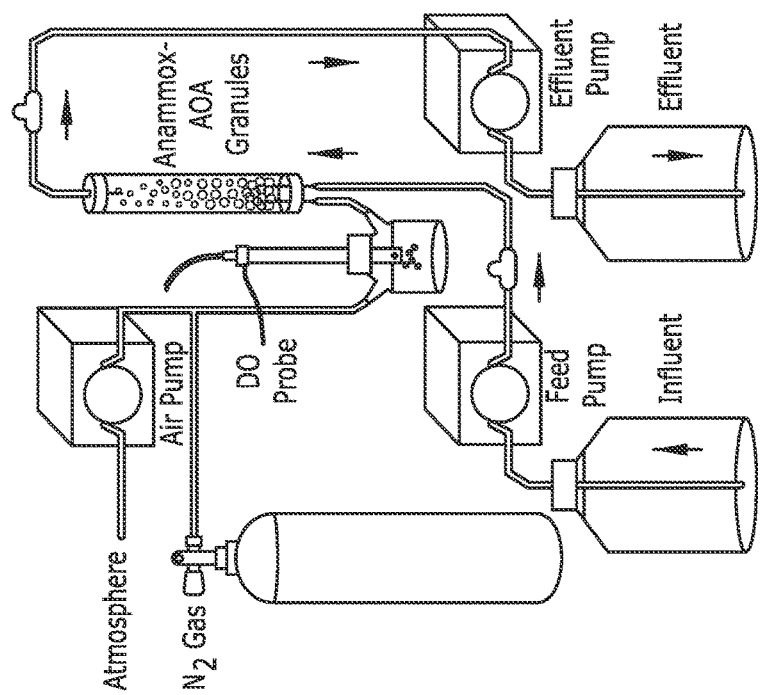
FIG. 6B
FIG. 6A

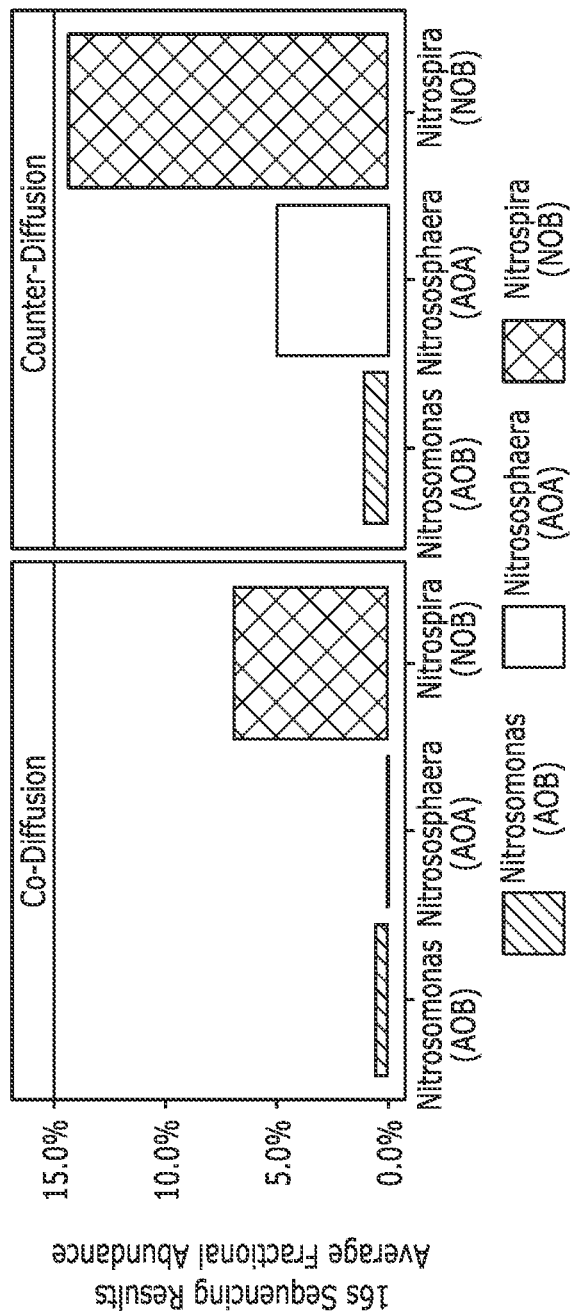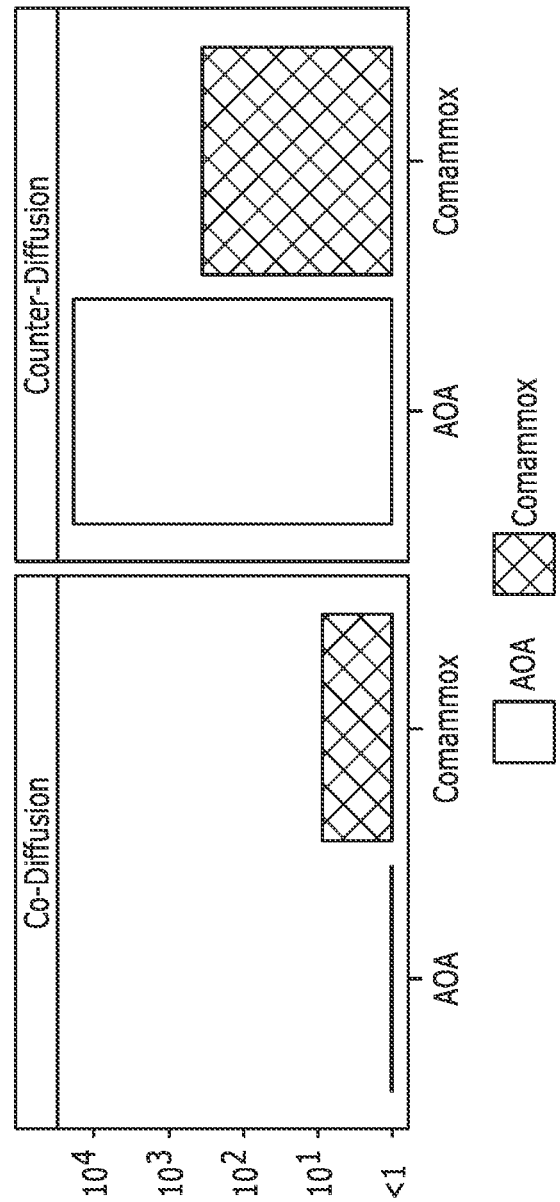

SEQUENCE LISTING

<160> NUMBER OF SEQ ID NOS: 2

<210> SEQ ID NO 1
<211> LENGTH: 19
<212> TYPE: DNA
<213> ORGANISM: Artificial sequence
<220> FEATURE:
<223> OTHER INFORMATION: Synthetic

<400> SEQUENCE: 1
gtgycagcmg ccgcggtaa                                            19

<210> SEQ ID NO 2
<211> LENGTH: 20
<212> TYPE: DNA

```
<213> ORGANISM: Artificial sequence
<220> FEATURE:
<223> OTHER INFORMATION: Synthetic

<400> SEQUENCE: 2
ccgycaatty mtttragttt                                               20
```

MICROBE-BASED SYSTEMS, COMPOSITIONS, AND METHODS THEREOF

CROSS REFERENCES TO RELATED APPLICATIONS

This application is a National Stage of International Application No. PCT/US2021/013127, filed Jan. 12, 2021, which claims the benefit of U.S. Patent Application No. 62/960,494, filed Jan. 13, 2020, the disclosure of each is expressly incorporated herein by reference in its entirety.

STATEMENT OF GOVERNMENT LICENSE RIGHTS

This invention was made with government support under Grant No. HR0011-17-2-0064, awarded by the Defense Advanced Research Projects Agency. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is UWOTL173217_Sequence_Listing_final_20210112.txt. The text file is 1 KB; was created on Jan. 12, 2021; and being submitted via EFS-Web with the filing of the specification.

BACKGROUND

The discharge of excess nitrogen from wastewater treatment plants has devastated aquatic communities by causing large eutrophication and algal blooms, a phenomenon that costs $2.2 billion annually in the U.S. alone. Nitrogen removal in water resource recovery facilities (WRRFs) is expensive due to high energy demand, sludge production, and, if the carbon to nitrogen ratio is too low, externally-purchased additional carbon. Partial nitritation/anammox has the potential to lower nitrogen removal costs and has already been successful in niche applications. Anammox aerobically oxidize ammonium with nitrite as the electron acceptor to form nitrogen gas, shortcutting the nitrogen cycle. Anammox require partial-nitritation by ammonium oxidizing bacteria (AOB), which oxidize ammonium, supplying nitrite ($NO_2^-$) for anammox. This partnership can lower aeration demand by more than half, reduce sludge production by up to 90%, and eliminate the need for external carbon, but requires suppressing the activity of nitrite oxidizing bacteria (NOB) with a low dissolved oxygen concentration that impacts the ability of AOB to reliably supply nitrite to anammox, lowering the overall nitrogen removal rate. This limitation has necessitated a search for a new method to reliably supply nitrite to anammox.

Anthropogenic nutrient input to marine systems due to human activities has also resulted in an increased incidence of Oxygen Minimum Zones (OMZs) which has expanded the ecological niche for both denitrifiers and anammox, two organisms capable of producing nitrogen gas under anoxic conditions, and two primary sources of marine gaseous nitrogen production. Both theoretical models and in situ measurements have suggested anammox is responsible for 30-50% of net nitrogen loss in the ocean, and in some regions, anammox activity rates are even higher.

Anaerobic ammonia oxidation (anammox), is an autotrophic metabolism performed by five candidate genera within the Plantomycetes phylum: *Brocadia, Kuenenia, Anammoxoglobus, Jettenia*, and *Scalindua*. Ammonia and nitrite are consumed in a ~1:1.3 molar ratio to produce one mole nitrogen gas and 0.3 moles nitrate, resulting in ~13% of the original nitrogen as nitrate. Ammonia is abundant in nature, but the anammox electron acceptor, nitrite, must be produced to sustain anammox activity, which is most commonly supplied by aerobic ammonia oxidizing bacteria and/or archaea (AOB, AOA).

AOA and anammox cooperate near the boundary of OMZs where oxygen diffuses downward from the surface while mineralized ammonia originating from within the OMZ diffuses upward toward the boundary. This counter-diffusion of substrate results in low ammonia and high oxygen concentrations on the oxygenated side of the OMZ boundary where AOA consume oxygen and produce nitrite. On the anoxic side of the OMZ boundary, anammox receive nitrite from AOA and thrive in the higher ammonia concentrations originating deep within the OMZ. These counter-diffusive fluxes offer a favorable environment for AOA-anammox co-operation, as anammox have a high affinity for nitrite ($K_{NO2,AMX}$=~48 µM) and AOA possess high affinities for both total ammonia and oxygen ($K_{NH3+NH4,AOA}$=~0.134 µM, $K_{O2,AOA}$=2-4 µM) as compared to AOB ($K_{NH4+NH3,AOB}$=~150 µM, $K_{O2,AOB}$=~15 µM).

Co-diffusion of ammonia and oxygen through a biofilm has been shown to favor a population of anammox and AOB in engineered settings. Worldwide, more than 200 wastewater treatment plants employ AOB-anammox-based nitrogen removal schemes in high ammonia digester centrate sidestreams where AOB and anammox grow together in spherical biofilms called granules. AOB grow on the granule periphery where they consume oxygen and convert ammonia to nitrite. Controlling the system at low dissolved oxygen (DO) (~10-75 µM) enables AOB and anammox to outcompete nitrite oxidizing bacteria (NOB) for oxygen and nitrite, respectively, due to poorer affinities of NOB for oxygen ($K_{O2,AOB}$=~0.5, $K_{O2,NOB}$=~0.9). The nitrite and residual ammonia then co-diffuse into the anoxic interior of the granule, where anammox convert ammonia and nitrite to di-nitrogen gas. AOB-anammox partnerships function well in the ammonia-rich sidestream (influent concentration >>10 mM $NH_4^+$, 1% of the volumetric flow). Due to major cost savings, it is appealing to apply anammox nitrogen removal to the ammonia deplete mainstream (influent concentration 2-5 mM $NH_3$, 99% of the volumetric flow). To suppress NOB, oxygen concentrations should remain low (<35 µM $O_2$), similar to marine OMZs. Because AOB growth rate is a function of both ammonia and oxygen concentrations, AOB activity drops at these low oxygen OMZ-like conditions and not enough nitrite is supplied to keep up with the stringent nitrogen removal requirements of the mainstream (<200 µM).

Despite NOB presenting substrate competition challenges for AOB/AOA-anammox partnership, a newly discovered complete ammonia-oxidizer (comammox) can produce nitrite under low oxygen conditions similar to AOA. One of the two available pure strains of Comammox, *N. inopinata*, exhibits a high affinity for ammonia ($K_{NH3}$≈0.63 nM), which is 4 to 2500 times lower than AOB), and 6 to 52 times lower than all known AOA except *Nitrosopumilus maritimus* ($K_{NH3}$≈3 nM $NH_4^+$). Meanwhile, *N. inopinata* demonstrates a poorer affinity for nitrite ($K_m$~372 µM $NO_2^-$) in comparison to many canonical NOB ($K_m$=9 to 27 $NO^-$), as well as anammox ($K_m$=48 µM $NO_2^-$), suggesting that the nitrite produced by *N. inopinata* is more likely to be consumed by other organisms than by itself. Comammox, like other *Nitrospira*, have been shown to be abundant in low oxygen concentration. A low oxygen lifestyle by other *Nitrospira* (*Nitrospira moscoviennensis*) can be explained by their ability to simultaneously consume nitrate and formate.

There is a need for systems that encourage growth and colonization of bacteria and archaea for use in a variety of applications such as wastewater nitrogen removal. The present disclosure fulfils these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a microorganism support structure, including a gas-permeable layer that includes two opposing surfaces; a microorganism adhesive, coating one surface of the layer; and a microorganism disposed on the microorganism adhesive-coated surface of the layer.

In another aspect, the present disclosure features a system, including a microorganism support structure that includes a gas-permeable layer including two opposing surfaces; a microorganism adhesive, coating one surface of the gas-permeable layer; and a microorganism disposed on the microorganism adhesive-coated surface of the gas-permeable layer; and a supply of a gas, wherein the gas is supplied from the surface opposite the surface coated with the microorganism adhesive.

In yet another aspect, the present disclosure features a method of using a system described herein, including continuously supplying a gas from the surface opposite the surface that has a microorganism disposed thereon, and continuously flowing a liquid over the surface having the microorganism disposed thereon.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIG. 6A is a schematic illustration of a small-scale co-diffusion setup. Air and $N_2$ gas were mixed before being filtered and fed into the co-diffusion environment.

FIG. 6B is a schematic illustration of a small-scale counter-diffusion setup. In the counter-diffusion environment, nitrogen gas was directly added to bulk liquid in a 2nd phase of operation.

FIG. 8A is a graph showing the relative abundance of aerobic nitrifiers in biofilms, after termination of operation of the co-diffusing environment (n=2), evaluated using 16S sequencing primer.

FIG. 8B is a graph showing the relative abundance of aerobic nitrifiers in biofilms, after termination of operation of the counter diffusing environment (n=1), evaluated using 16S sequencing primer.

FIG. 8C is a graph showing the relative abundance of aerobic nitrifiers in biofilms, after termination of operation of the co-diffusing environment (n=2), evaluated using qPCR primers.

FIG. 8D is a graph showing the relative abundance of aerobic nitrifiers in biofilms, after termination of operation of the counter-diffusing environment (n=1), evaluated using both 16S sequencing (top) and qPCR primers (bottom).

FIG. 15A is a phase contrast image of a microorganism support structure of the present disclosure, having microorganisms attached thereto, at 100× magnification;

FIG. 15B is a 630× magnification image of a portion of the microorganism structure of FIG. 15A; and FIG. 15C is a 630× magnification image of a portion of the microorganism structure of FIG. 15A.

DETAILED DESCRIPTION

Figure 1:
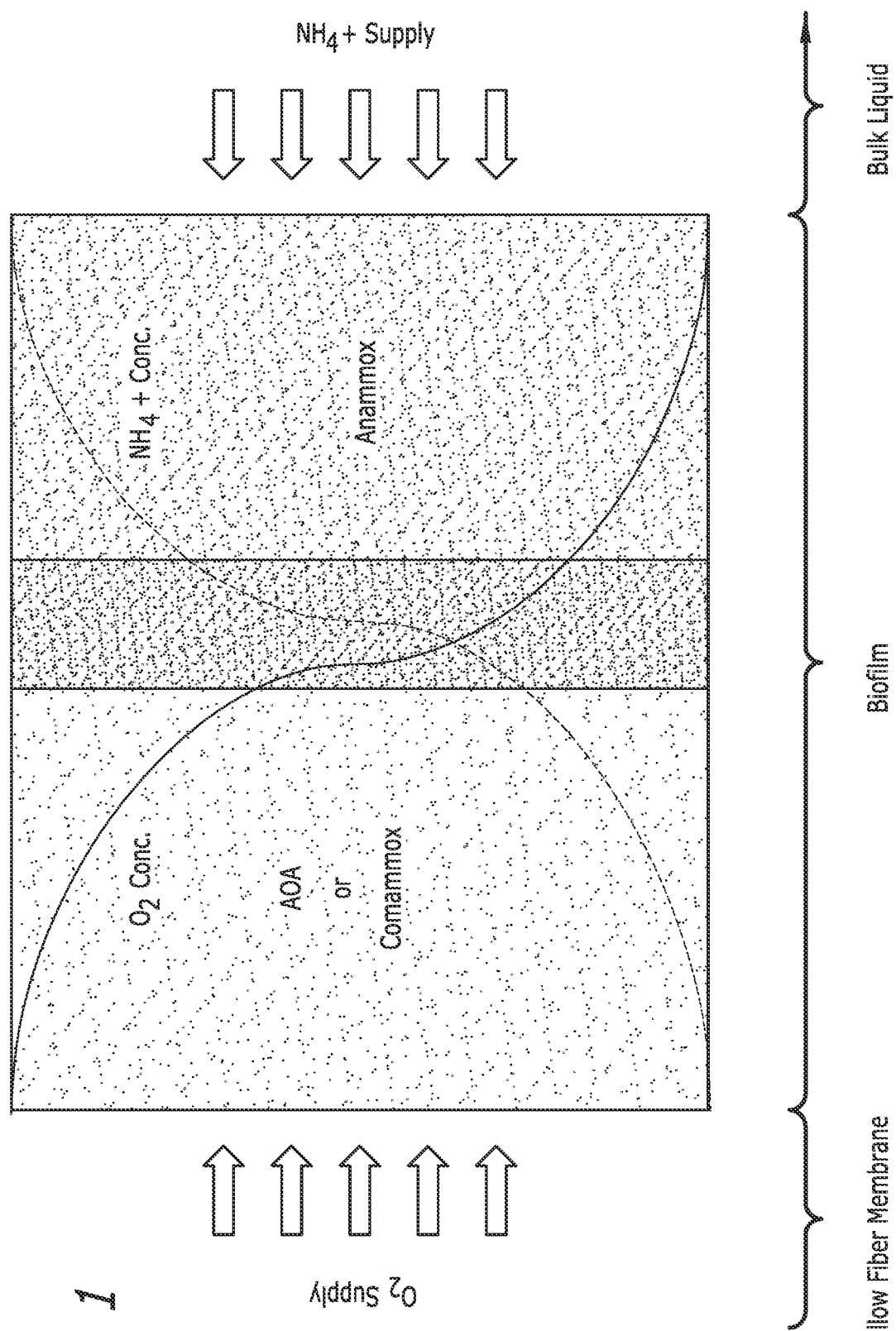
FIG. 1 is a schematic illustration of the flow of substrates through an embodiment of a model of a membrane aerated biofilm reactor (MABR). Oxygen and ammonium counter-diffuse across the biofilm resulting in high oxygen/low ammonium near the membrane, favorable to ammonium oxidizing organisms; and low oxygen/high ammonium near the bulk fluid, favorable to anammox which receive nitrite from the aerobic ammonium oxidizing species.

The present disclosure describes a microorganism support structure, including a gas-permeable layer that includes two opposing surfaces; a microorganism adhesive coating at least one surface of the gas-permeable layer; and a microorganism disposed on the microorganism adhesive-coated surface of the layer.

The microorganism adhesive enhances the adhesion of the microorganism on the gas-permeable layer compared to a gas-permeable layer that does not have the microorganism adhesive. In applications where microorganism support structure is employed, the support structure of the present disclosure maintains the viability of the microorganism disposed thereon and allows the immediate colonization of the microorganism and the use of the microorganisms that are supported by the structure.

Definitions

At various places in the present specification, substituents of compounds of the disclosure are disclosed in groups or in ranges. It is specifically intended that the disclosure includes each and every individual subcombination of the members of such groups and ranges.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable subcombination.

The verb "comprise" and its conjugations, are used in the open and non-limiting sense to mean that items following the word are included, but items not specifically mentioned are not excluded.

"About" in reference to a numerical value refers to the range of values somewhat less or greater than the stated value, as understood by one of skill in the art. For example, the term "about" could mean a value ranging from plus or minus a percentage (e.g., ±1%, ±2%, or ±5%) of the stated value. Furthermore, since all numbers, values, and expressions referring to quantities used herein are subject to the various uncertainties of measurement encountered in the art, then unless otherwise indicated, all presented values may be understood as modified by the term "about."

As used herein, the articles "a," "an," and "the" may include plural referents unless otherwise expressly limited to one-referent, or if it would be obvious to a skilled artisan from the context of the sentence that the article referred to a singular referent.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include 1 and 10, and any and all subranges between the minimum value of 1 and the maximum value of 10. Exemplary subranges of the range "1 to 10" include, but are not limited to, e.g., 1 to 6.1, 3.5 to 7.8, and 5.5 to 10.

As used herein, the term "random copolymer" is a copolymer having an uncontrolled mixture of two or more constitutional units. The distribution of the constitutional units throughout a polymer backbone can be a statistical distribution, or approach a statistical distribution, of the constitutional units. In some embodiments, the distribution of one or more of the constitutional units is favored. For a polymer made via a controlled polymerization (e.g., RAFT, ATRP, ionic polymerization), a gradient can occur in the polymer chain, where the beginning of the polymer chain (in the direction of growth) can be relatively rich in a constitutional unit formed from a more reactive monomer while the later part of the polymer can be relatively rich in a constitutional unit formed from a less reactive monomer, as the more reactive monomer is depleted. To decrease differences in distribution of the constitutional units, comonomers in the same family (e.g., methacrylate-methacrylate, acrylamide-acrylamido) can be used in the polymerization process, such that the monomer reactivity ratios are similar.

As used herein, the term "constitutional unit" of a polymer refers to an atom or group of atoms in a polymer, comprising a part of the chain together with its pendant atoms or groups of atoms, if any. The constitutional unit can refer to a repeat unit. The constitutional unit can also refer to an end group on a polymer chain. For example, the constitutional unit of polyethylene glycol can be —$CH_2CH_2O$— corresponding to a repeat unit, or —$CH_2CH_2OH$ corresponding to an end group.

As used herein, the term "repeat unit" or "monomeric unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "biodegradable" refers to a process that degrades a material via hydrolysis and/or a catalytic degradation process, such as enzyme-mediated hydrolysis and/or oxidation. For example, polymer side chains can be cleaved from the polymer backbone via either hydrolysis or a catalytic process (e.g., enzyme-mediated hydrolysis and/or oxidation).

As used herein, "biocompatible" refers to a property of a molecule characterized by it, or its in vivo degradation products, being not, or at least minimally and/or reparably, injurious to living tissue; and/or not, or at least minimally and controllably, causing an immunological reaction in living tissue. As used herein, "physiologically acceptable" is interchangeable with biocompatible.

As used herein, the term "anionic" describes the net negative charge of a material. It will be understood that a given negatively charged material may have one or more positively charged counterions associated with it, or vice versa. In solution a negatively charged material may have dissociated from one or more positively charged counterions with which it is associated. As used herein, the term "anionic" is used to describe a property of that material and not the overall complex with one or more counterions which will typically render the complex neutral. It is understood that certain functional groups are negatively charged, neutral or positively charged at varying values of pH. Whether a material is anionic will be determined based on the sum of these charges. Accordingly, at a given pH, if a material has one positively charged functional group and two negatively charged functional groups, then the material has a net negative charge and is anionic as the term is used in the context of the present invention.

As used herein, the term "cationic" refers to a molecule having a net positive charge. In the case of polymers, the term "cationic polymer" refers to a polymer having a net positive charge.

As used herein, a "hydrogel" refers to a network of crosslinked polymer chains that are hydrophilic, sometimes found as a colloidal gel in which water is the dispersion medium. A three-dimensional solid results from the hydrophilic polymer chains being held together by cross-links. The crosslinks which bond the polymers of a hydrogel fall under two general categories: physical and chemical. Physical crosslinks consist of hydrogen bonds, hydrophobic interactions, and chain entanglements (among others). Because of the inherent cross-links, the structural integrity of the hydrogel network does not dissolve from the high concentration of water. Hydrogels are highly absorbent (they can contain over 90% water) natural or synthetic polymeric networks.

As used herein, the term "derived from" or "derivative" refers to a molecule that is made from another molecule, with one or more substituents.

As used herein, the term "molecular weight" refers to the weight average molecular weight of the polymer chain in a polymer composition.

As used herein, "L-DOPA," "levodopa," "l-3,4-dihydroxyphenylalanine," or "3,4-dihydroxyphenyl-l-alanine" refers to

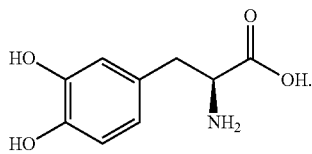 [SMILES: N[C@@H](Cc1ccc(O)c(O)c1)C(=O)O]

DOPA refers to L- and D-3,4-dihydroxyphenylalanine.

As used herein, "catecholamine" refers to an organic compound that has a catechol (benzene with two hydroxyl side groups next to each other) and a side-chain amine. Examples of catecholamines include dopamine, norepinephrine, epinephrine, adrenaline, isoproterenol, and dobutamine.

As used herein, "urushiols," "catechols," "catechins," and "pyrogallols" refer to phenolic compounds found in many plants, such as, for example, green tea.

As used herein, "peptide" refers to chains of between two and fifty amino acids, linked by peptide bonds (—NH—CO—).

As used herein, "polypeptide" refers to a linear organic polymer formed of many amino-acid residues bonded together in a chain.

As used herein, the terms "microbe", "microbial cell", or "microorganism" refer to an organism of microscopic, sub-microscopic, or ultramicroscopic size that typically has a single cell. Examples of microorganisms include bacteria, fungi, certain algae, and protozoa, and filamentous forms thereof. The term "microbial" indicates pertaining to, or characteristic of a microorganism.

The term "microbiome", as used herein, refers to a population of microorganisms from a particular environment, and includes the environment. The term is interchangeably used to address the population of microorganisms itself (sometimes referred to as the microbiota), as well as the collective genomes of the microorganisms that reside in the particular environment. The term "environment," as used herein, refers to all surrounding circumstances, conditions, or influences to which a population of microorganisms is exposed. The term is intended to include environments in a subject.

As used herein, adhering refers to surface attachment of the microorganism through physical entrapment, electrostatic interactions or bonds, or covalent bonds. Adhesion is a process that allows microorganisms to attach or adhere to other cells and surfaces. Adhesion is an important step for colonization of a new host or environment.

As described herein, "wastewater" includes water obtained from any source that requires treatment. For example, the wastewater may be obtained from or include one or more of water from or associated with wastewater treatment processes, fresh water, and aquatic mediums, among other sources. Industrial wastewater means water that carries waste from industrial or commercial processes and may include contaminated storm water and/or leachate from solid waste facilities. Municipal wastewater is collected wastewater from two or more sources wherein wastewater is generated by human activity including, but not limited to, human and animal excrement; domestic, commercial, agricultural, mining and industrial wastes and drainage; storm runoff; foodstuffs; and product, intermediate and raw materials disposal. Municipal wastewater can contain dissolved organics, solids, and various ions including ammonium cation and phosphorus-containing anions.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the FIGURES should not be viewed as limiting. It should be understood that other embodiments may include more or less of each element shown in a given FIGURE. Further, some of the illustrated elements may be combined or omitted. Yet further, an example embodiment may include elements that are not illustrated in the FIGURES.

Microorganism Support Structure

As described above, the present disclosure describes a microorganism support structure, including a gas-permeable layer that includes two opposing surfaces; a microorganism adhesive coating at least one surface of the gas-permeable layer; and a microorganism disposed on the microorganism adhesive-coated surface of the layer.

The material for the gas-permeable layer is not limited, so long as it is permeable to gases. In some embodiments, the gas-permeable layer is permeable to a gas, such as oxygen, methane, hydrogen, carbon dioxide, carbon monoxide, nitrous oxide, nitric oxide, and/or hydrogen sulfide. In some embodiments, the gas-permeable layer has a gas permeability coefficient of greater than 0.1 Barrer at 25° C.

The gas-permeable layer can be formed of a polymeric and/or ceramic material. The layer can be flexible. The polymeric material can include polypropylene, (high density) polyethylene, silicone, polyimide, polytetrafluoroethylene, polyvinylidene fluoride, cellulose acetate, polysulfone, polycarbonates, polyphenyl oxide, cellulose derivatives, poly(ethylene oxide), polybenzodioxanes, poly (butylene terephthalate), poly(ether-block-ester), polyacrylonitrile, polyethersulfone, polyvinyl alcohol, regenerated cellulose, polymethylmethacrylate, or a combination thereof. The ceramic material can include aluminum oxide/alumina, silicon carbide, titanium dioxide/titania, and/or zirconium dioxide/zirconia.

The gas-permeable layer can be free-standing, such that the layer is able to hold its shape without the need for an additional substrate or surface. In certain embodiments, the free-standing gas-permeable layer is connected, attached, or otherwise coupled to a surface or other object. However, the presence of the surface or other object is not required for the free-standing layer to maintain structural integrity. The gas-permeable layer can be resistant or impervious to thermal and chemical attack. For example, the gas-permeable layer can maintain its chemical and physical structure when exposed to a temperature of from 2° C. (e.g., from 5° C., from 10° C., from 15° C., from 20° C., from 25° C., from 40° C., from 50° C., or from 60° C.) to 65° C. (e.g., to 60° C., to 50° C., to 40° C., to 25° C., to 20° C., to 15° C., to 10° C., or to 5° C.) for a period of at least 1 month, and/or to a pH of from 1 to 14, for a period of at least 1 month.

In some embodiments, the gas-permeable layer is porous, and the pores can have a maximum dimension of from 10 nm (e.g., from 100 nm, from 250 nm, from 500 nm, or from 750 nm) to 1000 nm (e.g., to 750 nm, to 500 nm, to 250 nm, or to 100 nm). The gas-permeable layer can have a high surface porosity of 50% or greater (e.g., 60% or greater, or 70% or greater) and/or 80% or less (e.g., 70% or less, or 60% or less). In certain embodiments, the gas-permeable layer is in the form of a membrane, which can be in the form of, for example, a hollow tube, a flat sheet, or a spiral-wound membrane.

In some embodiments, when the gas-permeable layer is in the form of a hollow tube, the microorganism adhesive-coated surface and the microorganism disposed thereon is on the outer surface of the hollow tube. In certain embodiments, the hollow tube can have a diameter of from 0.1 mm (e.g., from 0.5 mm, from 1 mm, or from 2 mm) to 3 mm (e.g., to 2 mm, to 1 mm, or to 0.5 mm).

In some embodiments, the gas-permeable in the form of a flat sheet or a membrane can have a thickness of from 0.1 mm (e.g., from 0.2 mm, from 0.3 mm, or from 0.4 mm) to 0.5 mm (e.g., to 0.4 mm, to 0.3 mm, or to 0.2 mm).

The microorganism adhesive can include a polymer (e.g., a synthetic polymer, a polypeptide (natural or synthetic)) and/or a small molecule. For example, the microorganism adhesive can include polylysine, polymerized catecholamines such as dopamine, 3,4-dihydroxyphenyl-l-alanine (L-DOPA), 3,4-dihydroxyphenyl-l-alanine-containing peptide, polymerized catechols (e.g., catechols such as urushiol, catechol, catechin, pyrogallol, and similar natural polyphenolic compounds), and/or combinations of these with polylysine or other polycationic substances such as chitosan. The polycation can be added alone or can be polymerized in situ when the surface layer is formed by polymerization of a monomer, such as catecholamine. The polycation can be attached to a surface previously modified with a polycatecholamine. In some embodiments, L-DOPA can provide an anionic surface, and a polycation can ionically associate with the L-DOPA to provide a cationic surface. The microorganism adhesive can provide a cationic surface, anionic surface, and/or provide a specific binding moiety to the surface which the microorganism of interest will adhere to. In some embodiments, the microorganism adhesive includes polylysine, 3,4-dihydroxyphenyl-l-alanine (DOPA), a 3,4-dihydroxyphenyl-l-alanine-containing peptide, or any combination thereof. In some embodiments, the microorganism adhesive is a polypeptide, such as polylysine, polyarginine, polyalanine, polyglutamine, polyornithine, polyglutamic acid, polyaspartic acid, polyhistidine, or any combination thereof. In certain embodiments, the microorganism adhesive is polylysine. The polypeptide can have a molecular weight of greater than 30,000 Da (e.g., greater than 40,000 Da, greater than 50,000 Da, or greater than 60,000 Da).

The microorganism adhesive can coat one surface of the gas-permeable layer. In certain embodiments, both surfaces of the gas-permeable layer can be coated with the microorganism adhesive. The microorganism adhesive can have a thickness of 10 nm or more (e.g., 20 nm or more, 50 nm or more, 100 nm or more, 500 nm or more, 1 μm or more, 5 μm or more, 10 μm or more, 50 μm or more, 100 μm or more, 1 mm or more, 2 mm or more, 3 mm or more, or 4 mm or more) and/or 5 mm or less (e.g., 4 mm or less, 3 mm or less, 2 mm or less, 1 mm or less, 100 μm or less, 50 μm or less, 10 μm or less, 5 μm or less, 1 μm or less 500 nm or less, 100 nm or less, 50 nm or less, or 20 nm or less) on the gas-permeable layer.

The microorganism adhesive can be coated onto a surface of the gas-permeable layer by dissolving the microorganism adhesive in a solvent to provide a solution, and applying (e.g., spraying, dipping, flowing over, brushing, or any suitable method) the solution to the gas-permeable layer. The solvent can be removed after application of the solution, for example, by air-drying, applying a flow of a gas over the coated gas-permeable layer, heating, lyophilizing, removing the solvent under reduced pressure, and/or any suitable method for removing solvents. In some embodiments, the microorganism adhesive can be applied to the surface by in situ polymerization from a solution (e.g., an aqueous solution) containing a monomer (e.g., a catecholamine).

In some embodiments, the microorganism is attached to the microorganism adhesive-coated surface of the gas-permeable layer, such that the microorganism adheres to the surface in a strong enough affinity so as not to be washed off in a functioning wastewater reactor under normal operating conditions (e.g., at a pH value of from 3-9, a salt concentration of from 100 ppm to 35000 ppm, and a fluid pressure of from 14-300 psi). In some embodiments, the microorganism is firmly attached (e.g., through ionic interactions, and/or through physical entrapment in a matrix, such as a hydrogel matrix) to the microorganism adhesive-coated surface. The adhered microorganism can proliferate to provide a biofilm on the gas-permeable layer.

The microorganism can be applied to the microorganism adhesive-coated surface by dipping the adhesive-coated gas-permeable layer in a composition including the microorganisms (e.g., a suspension of microorganisms in a liquid, a polymeric suspension of microorganisms in a liquid), by spraying the adhesive-coated gas-permeable layer with a composition including the microorganisms, by brushing the adhesive-coated gas-permeable layer with a composition including the microorganisms, or any method suitable for introducing the microorganisms onto the adhesive-coated gas-permeable layer.

In some embodiments, the microorganisms can be in a matrix (e.g., a medium in which the microorganisms are embedded), such as a hydrogel material, and adhered to the microorganism adhesive-coated surface of the gas-permeable layer. In certain embodiments, the microorganism is directly adhered to the microorganism adhesive-coated surface of the gas-permeable layer, without any matrix material. The hydrogel material can include polyvinyl alcohol bearing styrylpyridinium group (SBQ-PVA), a positively-charged photocrosslinkable polymer that can ionically bond to a negatively charged microorganism adhesive-coated surface, such as a surface that has been coated with L-DOPA, or a L-DOPA-containing peptide. In some embodiments, the hydrogel material can include polyethylene imine, and/or chitosan that can interact and form hydrogels with a negatively-charged microorganism adhesive-coated surface, such as a surface that has been coated with L-DOPA, or a L-DOPA-containing peptide. In some embodiments, a negatively-charged hydrogel material can be further deposited over a positively-charged hydrogel material, such as cross-linked SBQ-PVA, polyethylene imine, and/or chitosan; or the negatively-charged hydrogel material can be deposited directly on a positively-charged microorganism adhesive-coated surface (e.g., a polylysine-coated surface). In some embodiments, the hydrogel material can include polyvinyl alcohol-based hydrogels, polyethylene glycol-based hydrogels, and/or alginate-based hydrogels. One or more of the hydrogel layer(s) can include a microorganism.

Once deposited on the microorganism adhesive-coated surface of the gas-permeable layer, the microorganism can remain viable and increase in biomass over time. In some embodiments, the microorganism-coated gas-permeable layer can be cultured in a suitable culture medium to provide a population of microorganism.

In some embodiments, the microorganism includes a single-celled organism, such as a bacterium, a fungus, an algae, a protozoa, or filamentous forms thereof. In certain embodiments, the microorganism includes an archaea, a bacterium, or a combination thereof. The microorganism, such as the archaea and/or the bacterium can consume a gas, such as $O_2$, $NH_3$, $CH_4$, $CO_2$, CO, NO, $N_2O$, and $H_2$, and can produce a compound such as $N_2$, methanol, polyhydroxyalcanoates, $CO_2$, $N_2O$, NO, and $NH_2OH$; or a compound derived from $N_2$, methanol, polyhydroxyalcanoates, $CO_2$, $N_2O$, NO, and $NH_2OH$.

In some embodiments, the microorganism includes bacteria or archaea that consume hydrogen, carbon, or nitrogen compounds (e.g., hydrogenotrophs, methanotrophs, denitrifying species), or any combination thereof. In some embodiments, the microorganism includes an ammonium-oxidizing archaea, a complete ammonia oxidizer bacterium, an anaerobic ammonium oxidation bacterium, or any combination thereof.

In some embodiments, the microorganism includes *Nitrospira*, species of ammonia-oxidizing Thaumarchaeota such as *Candidatus nitrosotenuis*, *Candidatus nitrosoarchaeum*, *Nitrososphaera viennensis*, *Nitrosopumilus maritimus*, *Nitrospira inopinata*, *Paracoccus denitrificans* Methylomonas sp. LW13, *Gemmatimonas auratiaca*, *Wollinella succinogenes*, *Nitrosomas europaea*, *Nitrosotenuis*, *Nitrosoarchaeum*, Ca. *Brocadia anammoxidans*, or any combination thereof.

The microorganism can be in the form of a biofilm, which refers to a syntrophic consortium of microorganisms in which cells stick to each other and to a surface. These adherent cells in the biofilm can be embedded within a slimy extracellular matrix that is composed of extracellular polymeric substances (EPSs). The cells within the biofilm can produce the EPS components, which can include a polymeric conglomeration of extracellular polysaccharides, proteins, lipids, and DNA.

Systems Including the Microorganism Support Structure

The present disclosure also features a system, including a microorganism support structure as described above, and a supply of a gas. The gas can be supplied from the surface opposite the surface on which the microorganism is disposed. For example, when the gas-permeable layer is a hollow tube and the microorganism adhesive-coated surface and microorganism disposed thereon are on the outer surface of the tube, the gas flows through the interior of the hollow tube and diffuse through the tube circumferential layer to the outer surface of the tube, such that the gas is supplied from the surface opposite the surface that is coated with the microorganism.

In some embodiments, the supplied gas is a substrate molecule for a first microorganism that is disposed on the microorganism adhesive-coated surface. For example, the supplied gas can include oxygen, $CH_4$, $N_2O$, NO, or $H_2$ or a combination thereof. The gas can be supplied at a pressure greater than atmospheric pressure. The first microorganism can consume the supplied gas and produce a product that can be consumed by a second, different microorganism.

In some embodiments, a second microorganism (different from the first microorganism) is disposed on the microorganism adhesive-coated surface. The second microorganism can consume a product produced by the first microorganism. The microorganisms on the microorganism adhesive-coated surface, such as the first and second microorganisms, can act in synergy to generate a product, such as nitrogen from ammonia in a wastewater stream.

In some embodiments, a liquid is in contact with the surface on which the microorganism is disposed. The liquid can supply a substrate molecule for the second microorganism that is different from the supplied gas and different from the product produced by the first microorganism. For example, the substrate molecule supplied by the liquid can include nitrogenous molecules (e.g., $NH_4^+$, $NH_3$, urea, $NO_2^-$, and/or $NO_3^-$), inorganic carbonaceous molecules (e.g., $HCO_3^-$), organic carbonaceous molecules (e.g., as acetate), and/or phosphate. The liquid can continuously flow over the surface on which the microorganism is disposed. In some embodiments, the liquid removes a product produced by the first microorganism, the second microorganism, or both the first and second microorganisms. In certain embodiments, the liquid is wastewater. In some embodiments, the substrate molecule for the second microorganism supplied by the liquid is ammonia.

In some embodiments, the system provides a counter-diffusive environment for the first and second microorganisms, such that the gas supplied from the surface opposite the surface on which the microorganisms are disposed decreases in concentration as a function of the distance from the gas-permeable layer; and the substrate molecule supplied by the liquid increases in concentration as a function of the distance from the gas-permeable layer. The first microorganism, which consumes the supplied gas, can decrease in population density and number as a function of the distance from the gas-permeable layer. The second organism, which consumes the substrate molecule supplied by the liquid and/or the product produced by the first organism, can increase in population density and number as a function of the distance from the gas-permeable layer.

The first and second microorganisms can each form a layer on the gas-permeable layer. The layer of the first or second microorganism can have a total thickness of from 10 μm (e.g., from 50 μm, from 250 μm, from 500 μm, from 1 mm, from 1.25 mm, from 1.50 mm, or from 1.75 mm) to 2 mm (e.g., to 1.75 mm, to 1.50 mm, to 1.25 mm, to 1 mm, to 500 μm, to 250 μm, to 50 μm). The layers of the first and second organism can have an overlapping interfacial layer, where both the first and second microorganisms are present. The overlapping interfacial layer can have a thickness that is from 5% (e.g., from 10%, from 25%, from 50%, from 75%) to 95% (e.g., to 75%, to 50%, to 25%, or to 10%) of the total thickness of the layers of the first and second microorganisms.

In some embodiments, when the liquid is wastewater, the wastewater contains ammonia, a substrate molecule for the second microorganism, and the system can convert the ammonia in the wastewater to nitrogen at an efficiency of greater than 90% that is sustained over a period of 3 months or more (e.g., 4 months or more, 6 months or more, 9 months or more, or 1 year or more).

In some embodiments, the first and the second microorganisms each independently includes an archaea or a bacterium. For example, the first and the second microorganisms can each independently include an ammonium-oxidizing archaea, a complete ammonia oxidizer bacterium, an anaerobic ammonium oxidation bacterium, or any combination thereof. In certain embodiments, the first microorganism is a complete ammonium-oxidizing bacterium and/or an ammonium-oxidizing archaea, and the second microorganism comprises an anaerobic ammonium oxidation bacterium. In some embodiments, the ammonium-oxidizing archaea includes *Nitrososphaera viennensis, Candidatus nitrosotenuis, Candidatus nitrosoarchaeum*; complete ammonium-oxidizing bacterium includes *Nitrospira* and *Nitrospira inopinata*, and the anaerobic ammonium bacterium includes a bacterium from the genera *Brocadia, Kuenenia, Anammoxoglobus, Jettenia,* or *Scalindua*.

In some embodiments, the system includes two or more species of bacteria and/or archaea that consume, exchange, or produce gases such as $H_2$, $CH_4$, $N_2$, $N_2O$, NO, and/or $O_2$. Representative species broadly encompass different phyla of bacteria (including the Proteobacteria, Firmicutes, Planctomycetes) and archaea (including the Euryarchaeota and Thaumarchaeota).

When the system is in operation, the gas can be continuously supplied from the surface opposite the surface having the microorganism(s) disposed thereof, and the liquid can be continuously flowed over the surface having the microorganism(s) disposed thereon.

The Examples below describes the microorganism support structures of the present disclosure, as well as systems incorporating the microorganism support structures.

EXAMPLES

Example 1: AOA/Anammox and Comammox/Anammox Membrane Aerated Biofilm Reactors Ammonium oxidizing organisms can supply anammox with nitrite. Ammonium-oxidizing archaea (AOA) have very low half saturation constants for both ammonium (0.133 μM for AOA and 79 μM for AOB) and oxygen (3.91 μM for AOA and 9 μM for AOB), making them uniquely suited to outcompete both AOB and NOB at low ammonium/low oxygen conditions found in the mainstream of water resource recovery facilities (WRRFs). The second organism, a complete ammonium oxidizing (comammox) bacterium, is unique because it is a single organism capable of oxidizing ammonium to ammonium and also oxidizing nitrite to nitrate. Nitrite is released extra-cellularly and then taken up again to produce nitrate. Like AOA, comammox have high affinities for oxygen (1.924 μM) and ammonium (0.65 μM), however their affinity for nitrite is low (450 μM) when compared to anammox (86 μM) making it a potential partner for Anammox.

Counter-diffusion can be facilitated by a new membrane-based system of the present Example, which allows for substrate to enter the biofilm in opposite directions across a biofilm. This can be accomplished in a Membrane Aerated Biofilm Reactor (MABR) that supply oxygen through a membrane instead of into the bulk liquid. The performance of anammox and these two ammonium oxidizing organisms, AOA and comammox, has not been explored in a MABR configuration to-date.

Referring to FIG. 1, in this configuration, oxygen is supplied through the hollow fiber membranes used in the reactor while ammonium is supplied from the bulk fluid, resulting in counter diffusion of the two key substrates required for nitrogen removal.

On the membrane side, the aerobic environment and low ammonium conditions are favorable to nitrifying species that prefer low ammonium conditions, such as AOA and comammox. On the bulk fluid side, oxygen has been consumed by the aerobic nitrifying population which supplies nitrite to the anammox that are thriving in the anaerobic ammonium-rich conditions present near the bulk fluid.

In the present Example, AOA and comammox were inoculated with anammox in two separate MABRs and each system's capacity for nitrogen removal was evaluated over time. These organisms could successfully supply anammox with nitrite, resulting in stable operation with high overall nitrogen removal.

Materials & Methods

Inoculation of Hollow Fiber Membranes

Cell concentration was measured by filtration of large volumes (1 L per culture) onto 2 μm track-etched polycarbonate membrane filters. For the AOA/anammox system, a mix of three different AOA strains was used, two freshwater strains (*N. candidatus* nitrosotenuis and *N. candidatus* nitrosoarchaeum) and one soil isolate (*N. viennensis*). For the comammox/anammox system, *N. inopinata* was used. Anammox granular sludge from a two-stage nitrogen removal system was masticated with an electric tissue grinder to create a dense dispersed mixture that could be easily attached to a hollow fiber membrane. Hydrogels may not coat the fibers evenly and may not be sufficiently stable. The olefinic fibers may not interact strongly with many hydrophilic materials but they do interact with poly-L-lysine. Other materials, as apparent to one skilled in the art, could be used to promote biofilm formation on such fibers.

All hollow fiber membranes were coated with ten layers of poly-L-lysine to enhance cell attachment to the fibers. Once the poly-L-lysine layer fully dried onto the membranes, it was submerged in a small volume (~25 mL) of concentrated aerobic ammonium oxidizing culture and allowed to incubate on a low RPM shaker for 30 minutes. After which, ~25 mL of the anammox mixture was added and allowed to attach to the membranes for another 30 minutes. The fibers where then inserted into the MABR system.

Design of Membrane Aeration Biofilm Reactors

Figure 2:
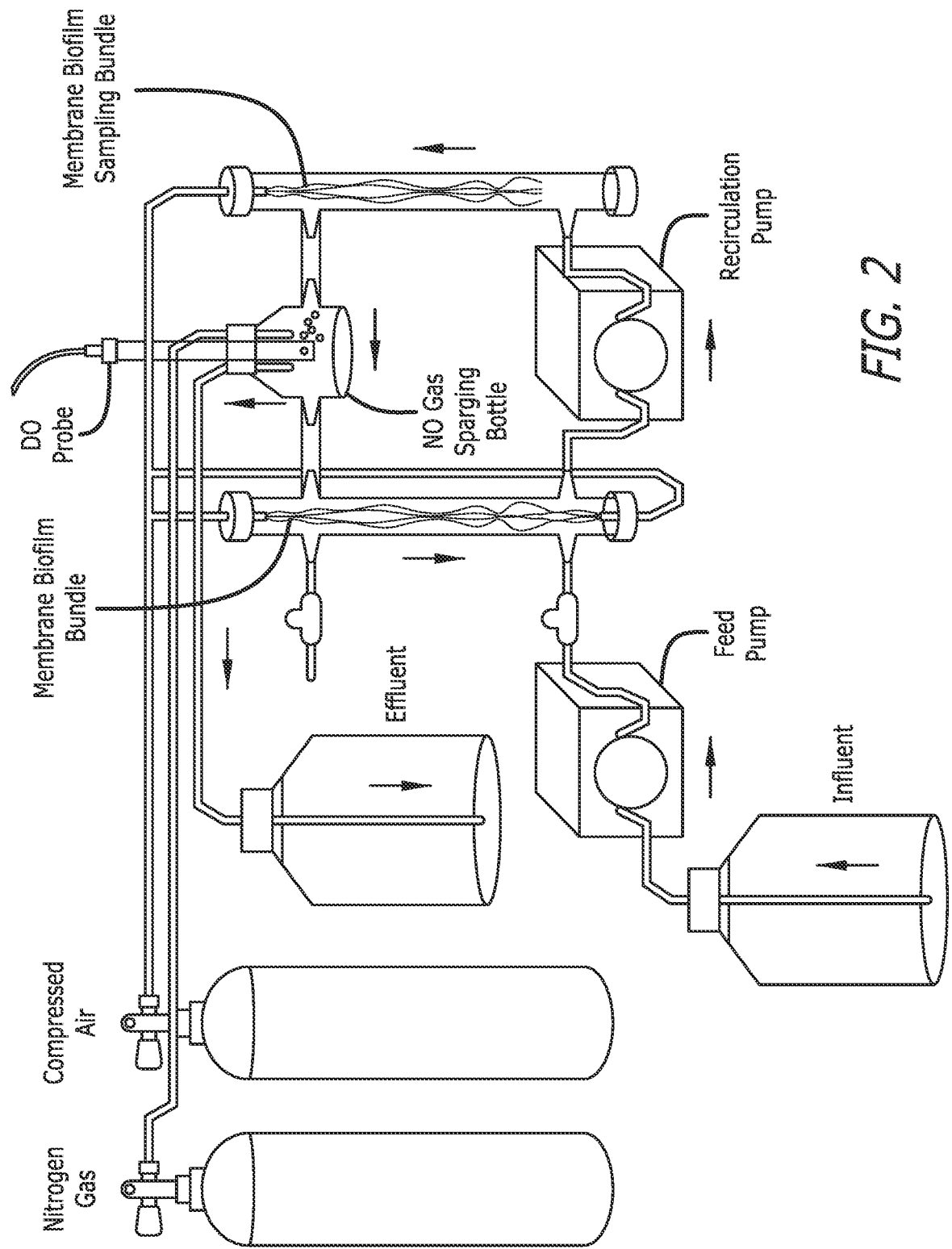
FIG. 2 is a schematic illustration of an embodiment of a single membrane aerated biofilm reactor operation.

Each reactor had two sets of hollow fiber membranes, one with both ends potted such that oxygen could flow freely through each strand, and the other with one end sealed and leak checked such that oxygen could enter the strand, but could only leave through the membrane fiber. This resulted in two membrane columns per reactor with 20 fibers each, for a total of four columns used in one embodiment. FIG. 2 shows the operation scheme of only one of the two reactors. In the first phase of the test, nitrogen gas was added directly to the media to ensure that anaerobic media only entered the column. In the second stage, this was revised, and nitrogen gas was added to the mixing bottle between the two columns. Dissolved oxygen (DO) was measured throughout the experiment. Consistent conditions in the bulk fluid were established by a 200 ml/min recirculation pump. Influent was fed through a pump at a rate of 15 ml/hr, the total reactor system volume was estimated to be about 400 mL. Effluent relied on gravity feeding to exit the system. Influent and effluent sampling was done at the three-way sample ports. Ammonium, nitrite, and total oxidized nitrogen measurements were taken three times per week with the Thermo Fisher Gallery Analyzer with assays bought from Thermo Fisher for the ammonium low, nitrite, and TON low (total oxidized nitrogen) tests. Nitrate concentration was calculated as the difference between total oxidized nitrogen concentration and nitrite concentration.

Results

Microscopic Staining and Visual Appearance

Figure 3:
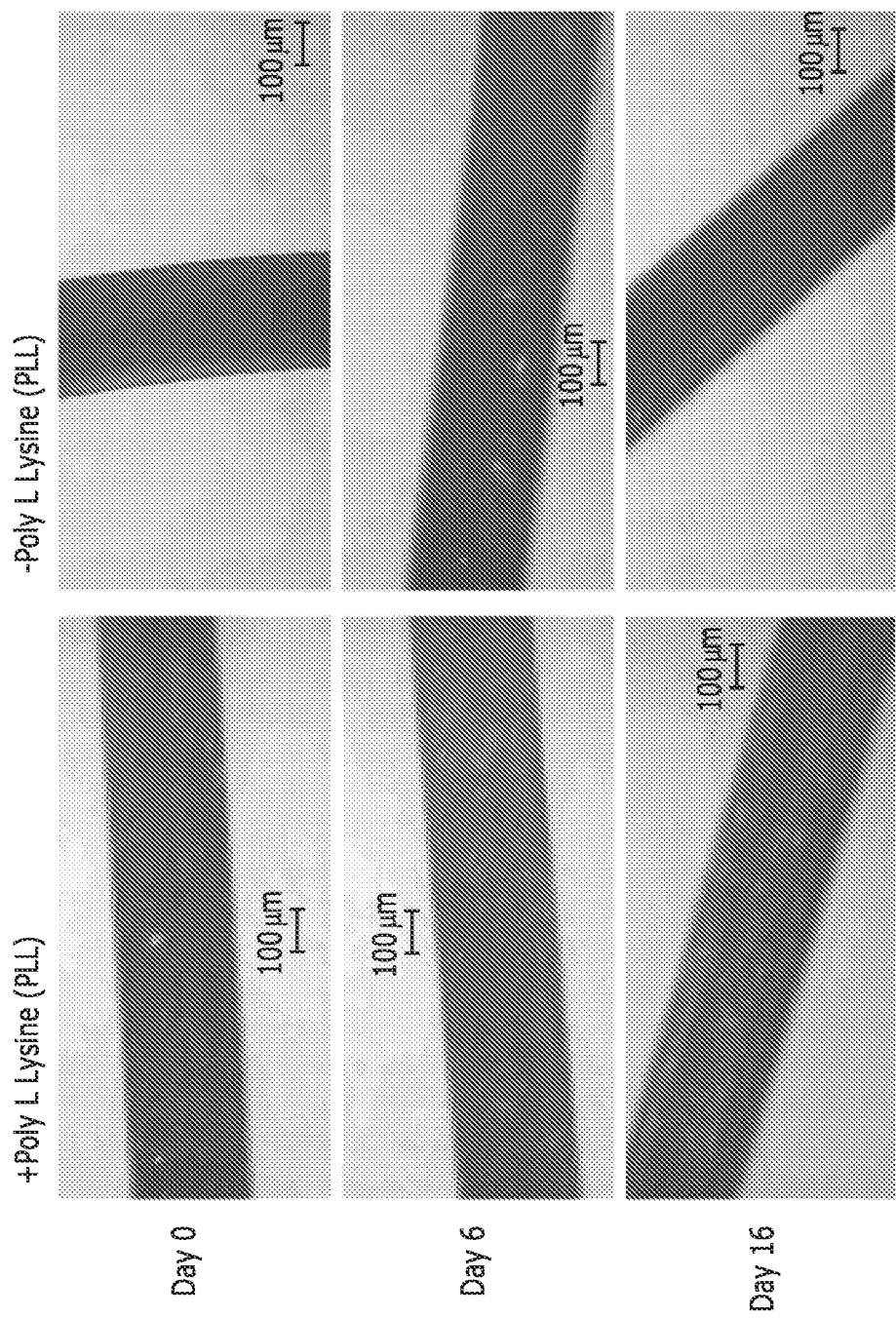
FIG. 3 is a series of photographs showing a bac-light viability assay performed on an embodiment of AOB-coated fibers with and without polylysine (PLL) at day 0, day 6, and day 16. From day 4 to day 16, $O_2$ is supplied to only the PLL treated fibers. Live biomass is indicated by light-colored shading (syto9 staining), dead biomass is indicated by darker shading (propidium iodide staining).

As shown in FIG. 3, individual fiber strands treated with PLL had a viable population from day 0 compared to the strands that were not treated with PLL. There were some dead cells at day 0, which could be attributed to the filtration process to concentrate the cells in a solution or due to the PLL. However, by day 6 and day 16 the presence of dead cells appeared to decrease, and the presence of live biomass seemed to increase.

Figure 4:
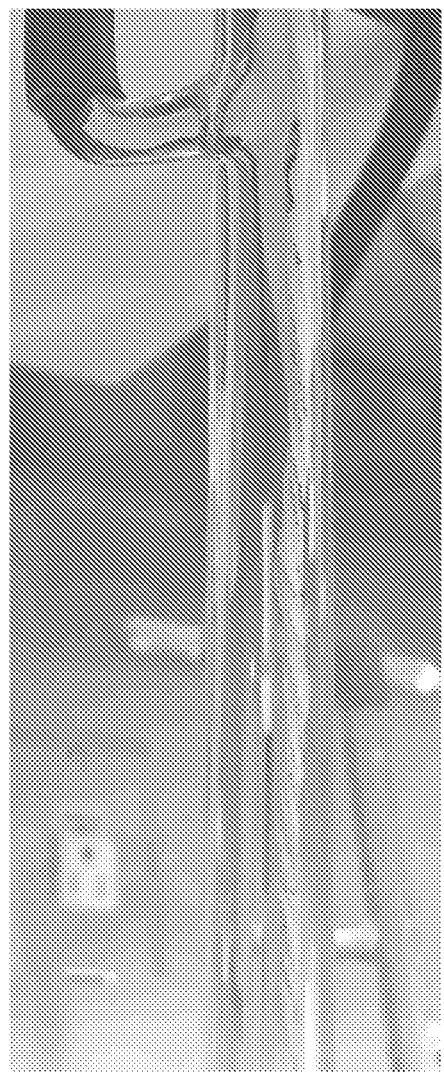
FIG. 4 is a photograph of visible biofilm seen on bundled fibers after 2 weeks in a bioreactor.

By the second week, a visible, black biofilm can be seen on the bundled fibers (FIG. 4). Thus, mounting AOB onto the membrane fibers using PLL was a success. This has also been tested with AOA and anammox layered biofilms.

Bioreactor Performance

Figures 5A, 5B:
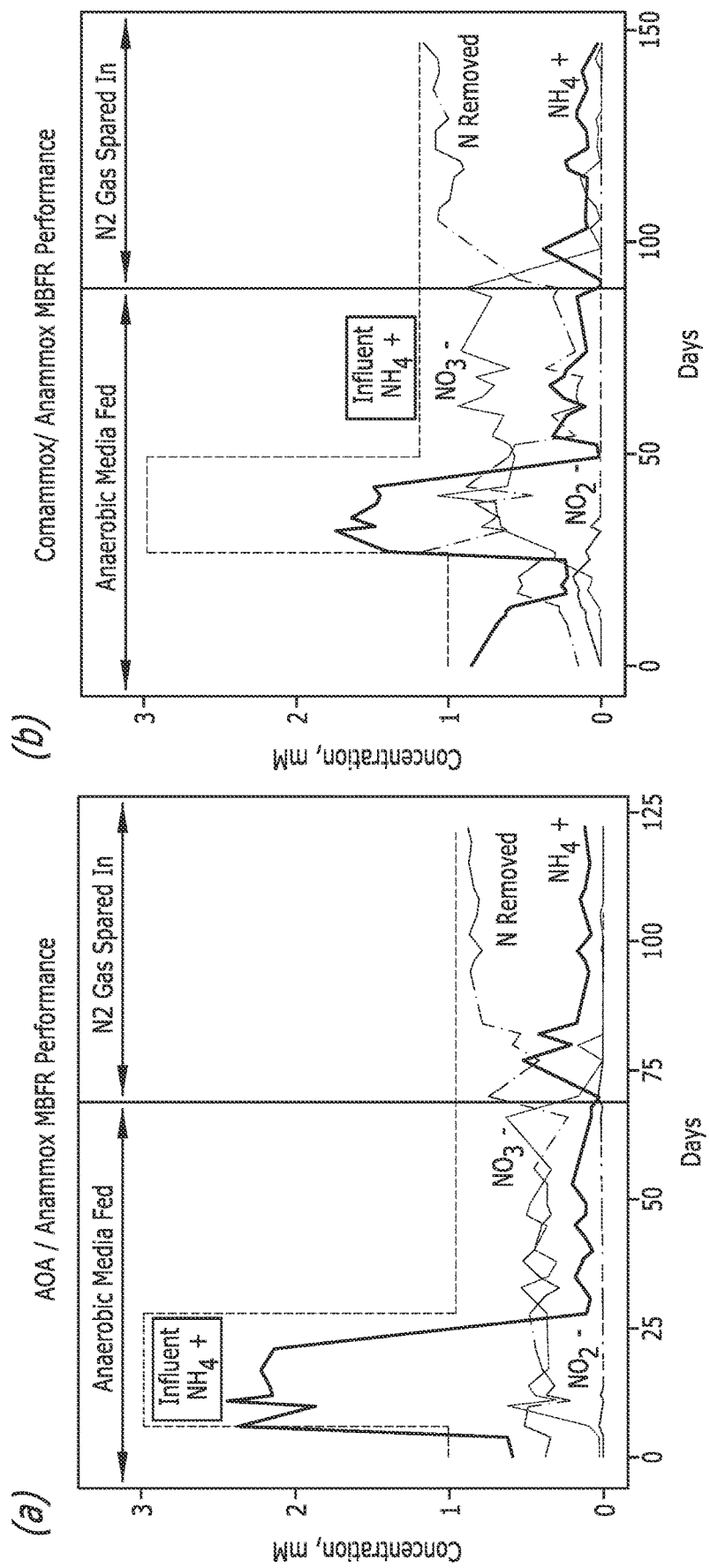
FIG. 5A is a graph of the performance of the AOA/Anammox MABR.
FIG. 5B is a graph of the performance of the Comammox/Anammox MABR.

Nitrogen removal and effluent concentration of nitrite, nitrate, and ammonium are shown in FIG. 5. At first, strong overall nitrogen removal was observed at relatively low loading rates, so the influent ammonium concentration was increased to encourage additional biomass production. However, this led to higher ammonium and nitrate concentrations in the effluent, so the influent ammonium concentration was lowered again. After lowering influent ammonium concentrations back down to the previous level, effluent nitrate concentration remained high, especially in the comammox system. This suggested the increased activity of nitrite oxidizing species, either NOB or comammox, in both systems. The higher nitrate concentration in the comammox/anammox system during this time was consistent with the initial inoculation of a nitrite oxidizing species, whereas this population required more time to develop in the AOA/anammox system. At this point, nitrogen gas was sparged directly into the circulating bulk fluid in the reactor (see FIG. 2). This ensured that the interface of biofilm and the bulk liquid would be anaerobic, providing anammox a larger fraction of anaerobic biofilm to grow in. This caused both systems to recover, with effluent ammonium, nitrite, and nitrate concentrations all becoming very small, and overall nitrogen removal was ~90% for both systems.

Thus, the capacity of AOA/Anammox and Comammox/Anammox pairs in a membrane aerated reactor both showed a high capacity to remove nitrogen over time (~90%).

Example 2: Elucidation of Partnerships Between Anammox, Ammonia Oxidizing Archaea, and *Nitrospira*

This Example compares the community compositions and fate of nitrogen within co-cultured aerobic and anaerobic ammonia oxidizing (anammox) microbial populations of both co-diffusing and counter-diffusing lab-scale microcosms. Typically, anammox metabolism leads to nitrate accumulation, however all ammonia was converted to nitrogen gas in both environments. 16S rRNA sequencing and qPCR using newly developed amoA primers for the Ammonium-Oxidizing Archaea (AOA) *Nitrososphaera viennensis* showed AOA was only present in the counter-diffusing environment while *Nitrospira* (including comammox) and anammox were abundant in both environments. FISH probes targeting *Nitrospira* showed high abundance in anoxic biofilm regions, suggesting some *Nitrospira* follow an anaerobic lifestyle. Given this unusual distribution and nitrate free effluent, it is believed that anammox supplied nitrate from its nitrogen removal pathway and formate from its $CO_2$ fixation pathway to *Nitrospira*, which used formate as an electron donor for anoxic nitrate reduction, in turn providing nitrite to anammox for removal. The novel comammox *Nitrospira inopinata* was also capable of this syntropy, consistent with the broader genera. The counter-diffusive microcosm replicated the syntrophic relationship observed in marine oxygen minimum zones where AOA, anammox, and *Nitrospira* cooperate to achieve complete ammoniacal nitrogen removal; a synergism which could lead to improved engineered systems.

In this study, nitrifier population dynamics and nitrogen removal in two types of redox-stratified synthetic microcosms was explored: co-diffusive and counter-diffusive. The co-diffusion system made use of granular sludge; the counter-diffusive system uses a hollow fiber membrane. In the counter-diffusive system, oxygen is fed through a hollow fiber membrane submerged in ammonia rich medium, resulting in substrates counter-diffusing across a biofilm that includes anammox and AOA. The established microenvironment mimics oxygen minimum zone (OMZ)-like conditions of oxygen diffusing into an ammonia-rich hypoxic/anoxic interior, demonstrating the viability of biomimicking a marine OMZ to improve nitrogen removal in wastewater treatment. To aid in the explanation of both low nitrate effluents from the microcosms and the presence of comammox in near anoxic conditions, trials were conducted on pure cultures of *N. inopinata* to evaluate comammox's use of formate under anoxic conditions for nitrate reduction.

Materials and Methods

Cultivation of Ammonia Oxidizing Organisms

Cultivation of strains was required prior to operation of the laboratory microcosms. AOA strains originating from shoreline sediment of Lake Acton (AC2) and Lake Delaware (DW1) were provided by Miami University. The AOA pure culture *Nitrososphaera viennensis* (DSM 26422) was received from DSMZ (Braunschweig, Germany). Suspended cultures of *N. viennensis* were maintained with an added 10 µM sodium pyruvate to enhance growth rate. All strains were maintained at 30° C. under low light conditions in 1 mM ammonia. A mineral salts media very similar to that used by Bollmann et al. was used, with exception of the trace elements solution (TES) and EDTA. Bollmann, A.; French, E.; Laanbroek, H. J. Isolation, Cultivation, and Characterization of Ammonia-Oxidizing Bacteria and Archaea Adapted to Low Ammonium Concentrations. *Methods Enzymol.* 2011, 486, 55-88, incorporated herein by reference in its entirety. Instead, 1 ml/L of the TES was used to grow *N. maritimus* and a 7.5 µM concentration of EDTA ferric sodium salt were supplemented. AOA were concentrated by filtration, collecting cells on 0.2 µm track-etched polycarbonate membrane filters from 1 L cultures.

Anammox was obtained from a granular sludge centrate treatment system of a wastewater treatment plant in Sluisjesdijk, Rotterdam, The Netherlands. Anammox granules for the co-diffusion environment were cultivated anaerobically at 36° C. For the counter-diffusion experiment, anammox granules were homogenized with a Bio-Gen (Cambridge, MA USA) Pro200 Electronic Tissue Grinder at 50% power for 1-2 minutes to create a dense dispersed culture, which could be sorbed to the modified hollow fiber membrane surface as described below.

Comammox *Nitrospira inopinata* was provided as a pure culture from the University of Vienna and grown planktonically in a limited mineral media with 1 mM $NH_4^+$ aerobically at 37° C. until almost all ammonium had been oxidized to nitrate at late exponential phase.

Design and Operation of Co-Diffusion Environment

Anammox granular sludge is a co-diffusing environment in which ammonium and oxygen diffuse together from the bulk liquid through the aerobic shell, where ammonium oxidizers grow, into the anoxic interior, where anammox grow. As such, a culture of AOA was concentrated and attached onto the surface of granular sludge. This was achieved through the adsorption of suspended culture AOA onto the surface of powdered activated carbon (PAC) which was subsequently adsorbed onto the surface of anammox granular sludge that had been cultivated under anaerobic conditions for six months. Prior to using the PAC (Thermo Fisher C272-500), it was thoroughly rinsed in 1% HCl and then in milliQ water, autoclaved, filtered (2.5 µm, Whatman 1442-110, Maidstone, UK) and dried at 100° C. overnight to minimize contaminants. To check the adsorption of AOA onto PAC, 100 mL of late-exponential phase DW1 culture was stained by adding 40 µL of a fluorescent nucleic acid stain, SYBR™ Green (Thermo Fisher, 57585) to the culture. After mixing and brief incubation (~60 seconds), 0.3 grams of PAC were mixed with stained culture using an autoclaved magnetic stir bar. A 20 µL sample was then examined on a microscope slide under a FITC filter. This was repeated after 24 hours.

PAC was added to anammox granular sludge and allowed a brief (~10 minutes) incubation time for adsorption. Unattached PAC was removed via tap water washes until the decant was relatively clear allowing 2 min of settling between washes. A sample of granules was kept on a shaker at 200 RPM for two weeks to evaluate the ability of PAC to remain on the granules.

A 0.5 mL aliquot of the AOA-enriched-PAC-dosed anammox granules was then placed in a 20 mL column, and continuously fed with sterile ammonia media (4.5 mL/hr). The influent ammonia concentration was adjusted until stable nitrogen removal rates were achieved at 1 mM influent. DO was maintained between 2-5 µM in all columns with filtered gas (0.3 µm, entry and exit filters) (FIG. 6A). Ammonia, nitrite, and nitrate were measured 3×/week. The chemical oxygen demand (COD) of the influent and effluent media was evaluated on days 72 (co-diffusion) and 31 (counter-diffusion) to check for denitrification activity.

Design and Operation of Synthetic Counter-Diffusion Environment

Composite hollow fiber membranes (STERAPORE™ Model No. 20M3400A, Mitsubishi Chemical, Tokyo, Japan) were potted in 1 cm diameter tubes with epoxy (1838 B/A green Scotch-Weld™, 3M, Saint Paul, MN USA) to seal the enclosure. To enhance cell attachment, fibers were coated with ten layers of poly-L-lysine. Once the poly-L-lysine layers fully dried, the membranes were submerged in ~25 mL of concentrated mixed AOA culture and allowed to incubate on a low RPM shaker for 30 min. Then, approximately 25 mL of the homogenized anammox mixture was added and allowed to attach to the membranes for another 30 minutes.

The system had two membrane modules, one double-ended membrane module, such that gas could flow freely through each strand, and one single-ended, such that gas could enter the one end, but only leave through the membrane fiber. Both modules had ~40 hollow fiber membrane strands (FIG. 6B). Compressed air supply to the membranes was kept between 1-2 psi. In the first phase of the experiment, nitrogen gas was connected to the pressure equalization vent on the media bottle to ensure anaerobic media was fed to this system. In the second phase, nitrogen gas was added to the mixing bottle between the two columns (FIG. 6B), ensuring an anaerobic boundary between the bulk liquid and the biofilm edge. In both phases, DO was measured at or below the detection limit (Vernier Optical DO Probe, Beaverton, OR USA). Homogeneous conditions in the bulk fluid were established by a 200 ml/min recirculation pump. Media was pumped at 15 ml/hr and the total system volume was ~400 mL. Sampling was done at three-way ports, shown in FIGS. 6A and 6B. Ammonia, nitrite, and nitrate were measured three times per week.

Molecular Techniques

Biofilm samples were stored for DNA extraction and fluorescent in-situ hybridization (FISH). The membrane fibers were removed from the reactor at the end of the experiment then cut into pieces. The granular sludge allowed sample collection throughout the experiment and granules were stored at days 0, 31, and 118 of operation. DNA was extracted using the DNeasy PowerBiofilm Kit (QIAGEN, Hilden, Germany) and quantified with both the Thermo Fisher NanoDrop 1000 Spectrophotometer and the Thermo Fisher Qubit dsDNA High Sensitivity assay. Illumina (MiSeq 2×300PE) sequencing of the V4-V5 region of the 16S rRNA gene using primers 515F-Y (5'-GTGY-CAGCMGCCGCGGTAA) [SEQ ID No. 1] and 926R (5'-CCGYCAATTYMTTTRAGTTT) [SEQ ID No. 2] with 20 k reads per assay, and was performed by Molecular Research Laboratories (Shallowater, TX USA). Analysis of sequencing data was performed with the USEARCH v11 package; unoise3 was used to select OTUs and taxonomy was assigned with the sintax command using the RDP 16S training database (release 11). Comammox and anammox presence were evaluated with qPCR using comammox amoB primers (148F and 485R) and 16S anammox primers (818F and 1040R). A standard for the anammox 16S rRNA gene was constructed by cloning the amplicon for the 808 to 1066 gene region using 808F and 1066R into the pCR™4-TOPO® TA vector (TOPO® TA Cloning® Kit, Invitrogen™, Carlsbad, CA USA) and validating the construct by sequencing (Eurofins Scientific, Luxembourg). For quantification of the comammox amoB gene, a plasmid containing the targeted sequence in Nitrospira inopinata was used as a standard.

Primers to identify the N. viennensis AmoA gene were selected by identifying conserved regions in the amoA gene after alignment of sequences with two other AOA strains, AC2 and DW1. Regions that contained at least two mismatches from the other two amoA sequences were selected for primer sequences. For each of the three amoA sequences, the complete gene sequence was synthesized and cloned within the pUC18 plasmid (BIOBASIC®). qPCR tests with all three plasmids showed specific amplification of the N. viennensis amoA gene by the primers. For quantification the pUC18-N. viennensis, amoA construct was used as a standard.

Samples for FISH were washed in phosphate buffered solution pH 7.0 (PBS) and soaked in 4% paraformaldehyde solution for 2 hours before being stored in a mixture of 98% ethanol and PBS. Three different probes designed to hybridize with Nitrospira were used per sample (Fluorescein, green), anammox (Cyanine 5, red), and general archaea (Cyanine 3, blue). Hybridization was done with 35% formamide hybridization buffer and 80 µM NaCl washing buffer.

Anoxic Processing of Formate by Comammox N. inopinata

Twenty mL of N. inopinata culture was used to inoculate 200 mL of commamox media supplemented with 1 mM sodium formate. After inoculation, the media was purged with nitrogen gas for 15 minutes to create an anoxic environment. Four replicates were used for one run; one control without formate and three biological triplicates with formate. Runs lasted between 1-10 days depending on activity.

Chemical Analysis

Ammonia, nitrite, and total oxidized nitrogen (TON) were determined with the Gallery Analyzer (Thermo Fisher, Waltham, MA USA). Nitrate was calculated as the difference between TON and nitrite concentrations. COD was calculated using the Hach™ (Loveland, CO USA) COD Digestion Vials, Low Range. Formate concentration was measured via ion chromatography, (Dionex™ ICS-5000+ Capillary HPIC™, Thermo Scientific™).

Results

Metabolite Concentrations in Co-Diffusion and Counter-Diffusion Microcosms

Figures 7A, 7B:
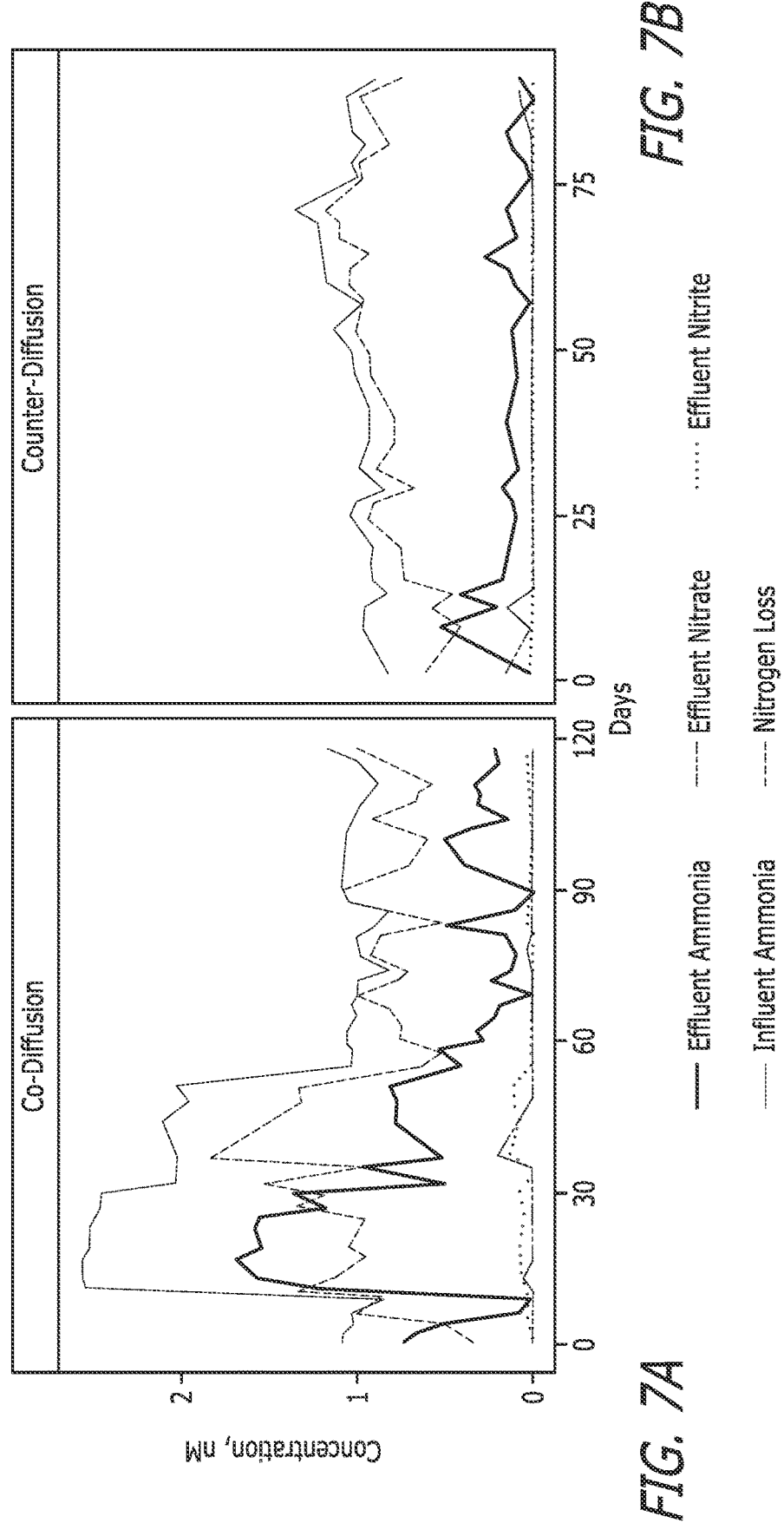
FIG. 7A is a graph showing the performance of AOA-inoculated anammox when ammonia was the only nitrogen source available in a co-diffusing environment (left).
FIG. 7B is a graph showing the performance of AOA-inoculated anammox when ammonia was the only nitrogen source available in a counter-diffusing environment (right). The measured nitrogen removed (-•-) was near the concentration of ammonia fed into the synthetic environment (-, grey), indicating a high rate of nitrogen loss in the system.

Effluent concentrations of the nitrogen species from both synthetic environments along with the fed ammonia concentration are shown in FIGS. 7A and 7B. The concentration of ammonia supplied to the co-diffusing synthetic environment was increased once nitrogen loss was near complete, to build up biomass of the co-culture. When effluent ammonia concentrations remained high, the influent ammonia concentration was stepped back down to promote an oligotrophic environment. The counter-diffusion system was fed anoxic media for 69 days with compressed air supplied to the hollow fiber membrane bundles. During that time, nitrate concentration in the effluent slowly increased. This was likely due to oxygen penetrating too far into the biofilm, which inhibited anammox growth. After 69 days, nitrogen gas was added directly to the bulk fluid, as is shown in FIG. 6B, to reduce DO in the bulk liquid, effectively decreasing the biofilm's aerobic fraction. After adding nitrogen gas, nitrogen removal dramatically improved and nitrate and nitrite effluent concentrations were minimal. FIGS. 7A and 7B show the performance during the $2^{nd}$ phase only. No consumption of COD was found when measurements were taken on day 72 for the co-diffusion or day 31 for the counter-diffusion environments. The counter-diffusion system averaged 90% nitrogen removal while the co-diffusion system averaged 76% removal during stable operation.

Microbial Populations in Co-Diffusion and Counter-Diffusion Microcosms

Figure 9:
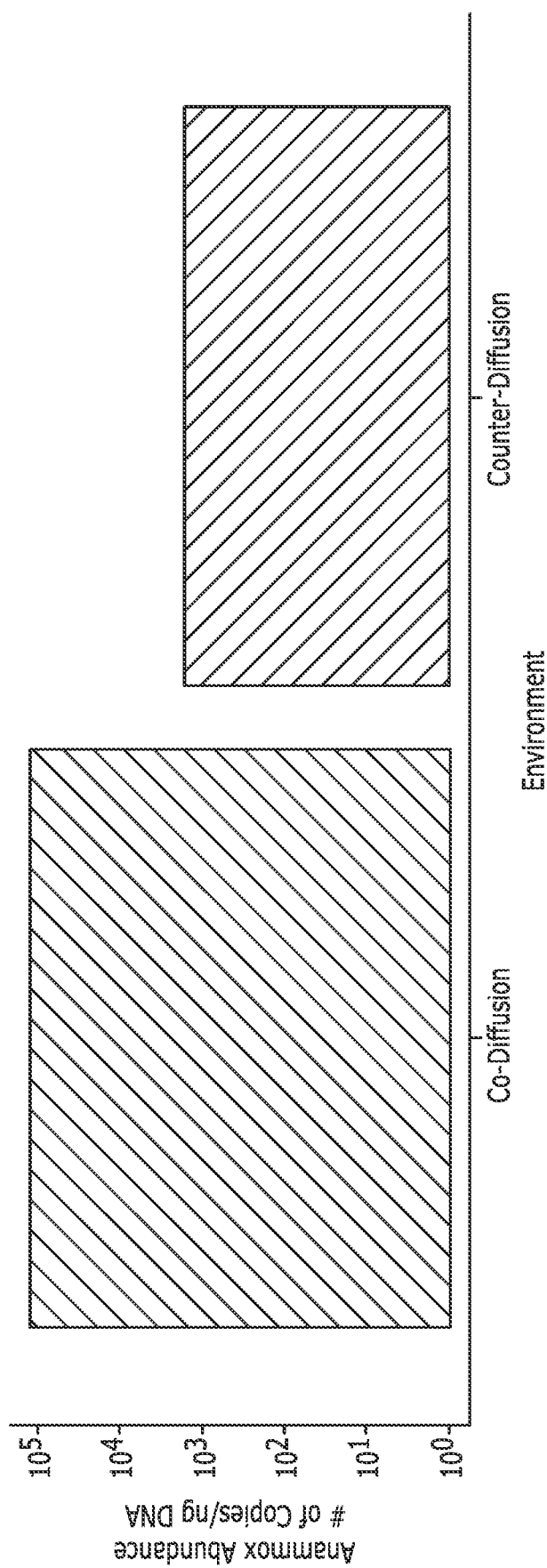
FIG. 9 is a graph of the absolute abundance of anammox measured in the biofilms of the co- and counter-diffusing environments after operation ceased, using qPCR primers designed to target the 16S rRNA gene of anammox.

Abundances for all aerobic nitrifiers in the biofilms were measured with both 16S rRNA gene sequencing and verified with qPCR after operation ceased (FIGS. 8A-8D). Both sequencing and qPCR demonstrated a high abundance of AOA as Nitrososphaera viennensis in the counter-diffusing environment and effective absence in the co-diffusing environment. Sequencing results indicated that prior to operation, ~10% of reads from the co-diffusing environment belonged to the inoculated AOA species. High abundance of an uncharacterized Nitrospira taxa were also found in the sequencing results for both systems. Since 16S rRNA gene sequencing does not provide enough resolution to differentiate between comammox Nitrospira and canonical NOB Nitrospira, qPCR was required to evaluate the presence of the amoB diagnostic of comammox. Low abundances of comammox were found in both environments when checked with qPCR using general primers designed to target all known Nitrospira amoB genes. Gel electrophoresis was performed with the qPCR product from the co-diffusion environment to confirm the amplicon size matched the expected target length The relative abundance of anammox measured via 16S rRNA gene sequencing was low (<2%) however qPCR amplification of the anammox 16S rRNA gene showed anammox was clearly present in both systems (FIG. 9). This discrepancy could be caused by primer bias in the 16S rRNA sequencing process which may select against anammox. This analysis also does not account for gene copy numbers, which has shown to be another source of error in 16S rRNA analysis. Assuming 1-4 fg DNA/cell, the qPCR results suggest a similar relative abundance to the those shown in 16S rRNA sequencing in the counter-diffusing environment (0.16-0.10%), and a potentially higher relative abundance than described in 16S sequencing in the co-diffusing environment (12-1.5%). The complex nature of the anammox cell wall, which has been shown to consist of an additional layer of peptidoglycan beneath the gram-negative outer membrane, may lower DNA extraction efficiencies, lowering the relative anammox abundances detected.

Microscopy of in Co-Diffusion and Counter-Diffusion Microcosms

Figures 10A, 10B:
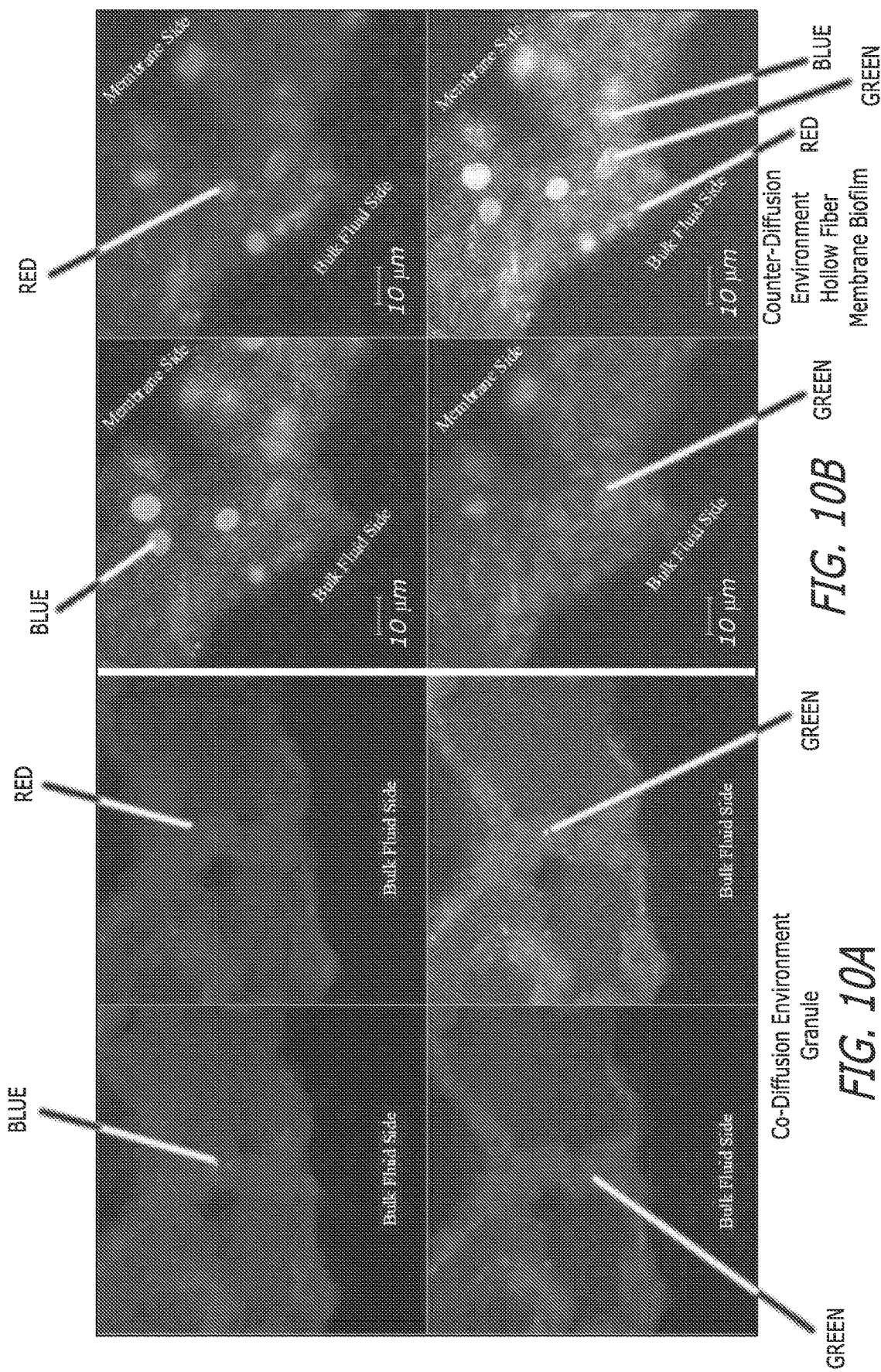
FIG. 10A is a series of FISH images of the biofilms present in the co-diffusing granular system. Archaea are stained with blue (cy5), Anammox cells are hybridized with red (cy3), and *Nitrospira* is stained with green (fluorescein).
FIG. 10B is a series of FISH images of the biofilms present in the counter-diffusion membrane system. Archaea are stained with blue (cy5), Anammox cells are hybridized with red (cy3), and *Nitrospira* is stained with green (fluorescein).

FISH was performed on a cross section of the granules present in the co-diffusing system (FIG. 10A) and a cross section of a membrane fiber in the counter-diffusing system (FIG. 10B). Anammox (red), and *Nitrospira* (green) were clearly visible in both systems while archaea (blue) were more abundant in the counter-diffusing system. A live/dead stain of the exterior of a segment of membrane fiber showed co-association of living cells, with dead cells on the exterior of the membrane and the highest concentration of live cells on the face of the membrane fiber facing toward the bulk fluid.

Anoxic Reduction of Nitrate by Comammox *N. inopinata*

Experimentation was conducted to elucidate the role of comammox, as one of multiple potential contributors, in lowering nitrate in effluents within anoxic synthetic environments. To evaluate whether comammox can produce nitrite from nitrate by a potential formate-oxidizing pathway, pure cultures of comammox with formate were tested in anoxic conditions.

Figure 11A:
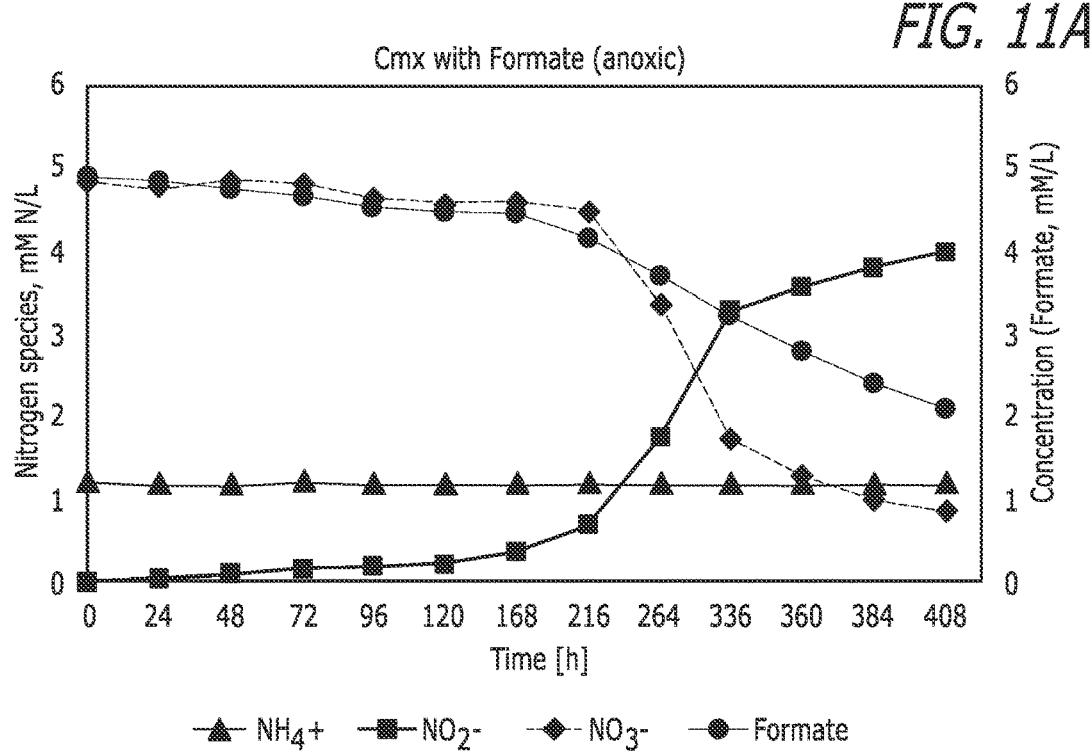
FIG. 11A is a graph showing the anoxic reduction of nitrate to nitrite using formate as an electron donor by the comammox *N. inopinata*: Nitrogen species transformation in cultures supplied with formate.
Figure 11B:
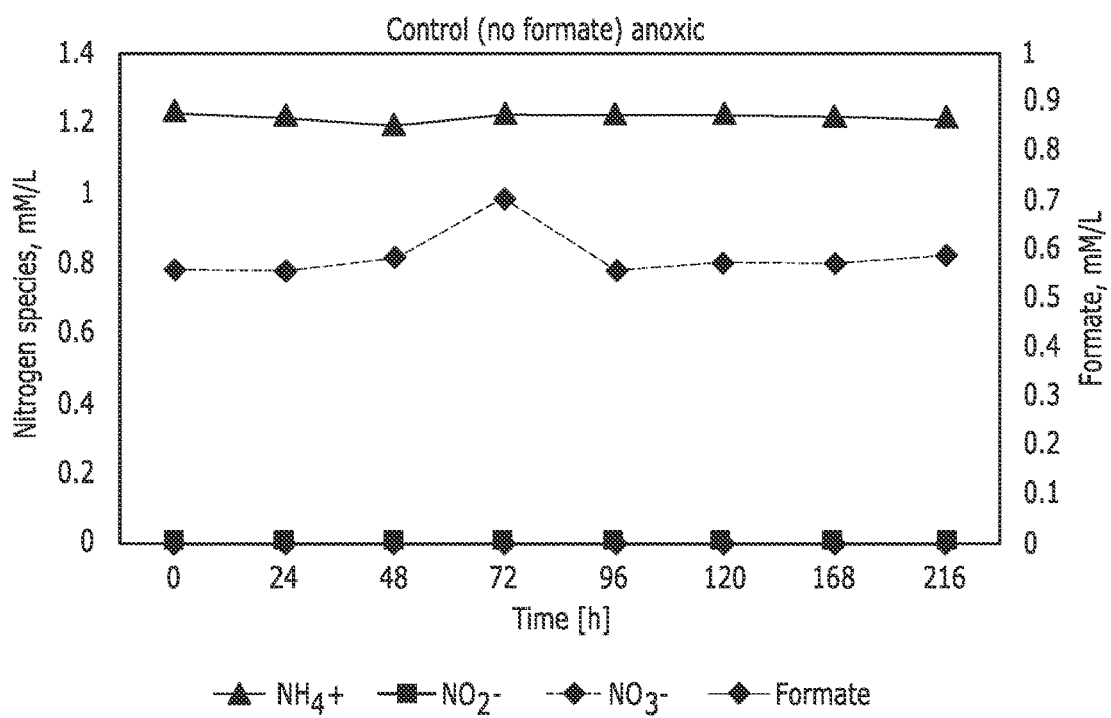
FIG. 11B is a graph showing the anoxic reduction of nitrate to nitrite using formate as an electron donor by the comammox *N. inopinata*: Nitrogen species transformation in cultures with no supplied formate.

*N. inopinata* showed strong evidence of nitrate reduction in the presence of formate (FIGS. 11A and 11B). Throughout the course of 408 hours, nitrate and nitrite are produced and consumed commensurately at a 1:1 ratio, while ammonium concentration remains constant. Formate was also consumed at a 1.3:1 ratio to nitrate (FIG. 11A), which is close to the stoichiometrically predicted 1:1 consumption of formate and nitrate and may indicate other means of oxidizing formate were present. The control, without formate, showed neither nitrite accumulation nor nitrate consumption. (FIG. 11B). The rate of nitrite production increases over time from 0.047 to 0.179 mM NO2-N/day over the duration of the experiment).

Nitrogen Removal by AOA and Anammox Requires Counter-Diffusion

The counter diffusive environment was designed to mimic conditions within a typical OMZ, where ammonia and oxygen are supplied from opposite directions, which can promote an AOA-anammox partnership. While both the counter- and co-diffusion synthetic environments were found to remove nitrogen autotrophically through anammox, AOA were only present in the counter-diffusion environment with surprisingly low AOB abundances (<2%) and high *Nitrospira* abundance (7-14%) in both systems (FIGS. 8A and 8B). FISH and qPCR analysis confirmed these findings (FIGS. 8C and 8D and FIGS. 10A and 10B). Thus, AOA outcompetes AOB in counter-diffusing systems because their high affinity for ammonia gives them a competitive edge. In the counter-diffusion system, anammox consume most of the ammonia diffusing in from the anaerobic bulk liquid and oxygen diffuses into the biofilm base attached to the hollow fiber membrane, resulting in low-ammonia/high-oxygen conditions near the base of the biofilm. Nitrogen removal is higher in this AOA-driven counter-diffusing environment because anammox continue to receive nitrite at lower ammonia concentrations. FISH microscopy of the biofilm (FIGS. 10A and 10B) supported this, as the brightest clusters of anammox (red) were densest near the anaerobic bulk liquid exposed biofilm edge. The AOA (blue) were more abundant near the middle and base of the biofilm, where oxygen concentrations supported aerobic ammonia oxidization by AOA.

Comammox Presence in Co-Diffusing and Counter-Diffusing Environments

The high abundance of an unidentified *Nitrospira* taxa (FIGS. 8A-8D) in both the co- (7%) and counter-diffusing (14%) environments was unexpected, given the low DO concentration measured in the co-diffusing environment (2-5 µM) and the absence of nitrate in the effluent of either system (FIGS. 7A and 7B). qPCR analysis indicates that a fraction of those *Nitrospira* included comammox. Co-operation between anammox and comammox has been observed in synthetic microcosms, where ammonia and oxygen co-diffuse together. Comammox was found to be present in both biofilm systems, with higher abundance in the counter-diffusing system (FIG. 8B).

Anoxic *Nitrospira* Activity

The copy numbers of comammox amoB detected with qPCR were lower than the abundances of *Nitrospira* detected with 16S rRNA gene sequencing, suggesting only a small fraction of *Nitrospira* present were capable of complete ammonia oxidation (FIGS. 8A-8D). For example, in the counter-diffusing environment, 5-fold copies of *N. viennensis* amoA were detected than comammox amoB, whereas the 16S rRNA gene sequencing results suggested *Nitrospira* was three times as abundant as AOA. It is possible the newly developed primers do not amplify all comammox organisms as more comammox species are still being discovered. However, even considering confounding factors (primer bias, differences in 16S rRNA gene copy numbers, etc.), the magnitude of the measured disparity cannot be ignored, and it is likely not all *Nitrospira* present were comammox. It also seems unlikely these *Nitrospira* were canonical NOB as the DO of the co-diffusion environment was controlled at 2-504, an order of magnitude lower than the reported affinity of *Nitrospira* for oxygen (~30 µM). FISH microscopy results show the *Nitrospira* (green) were relatively uniformly distributed across oxic (AOA-rich) and anoxic (anammox-rich) regions of the biofilm (FIG. 9).

Although *Nitrospira* and other NOB have traditionally been considered obligate aerobes, they are capable of anaerobic metabolisms as well. *Nitrospira moscoviensis* can reduce nitrate to nitrite, using formate as an electron donor by reversing the activity of its nitrite oxidoreductase (NXR) enzyme. *Nitrospira inopinata* is assumed to possess a periplasmic nitrate reductase (nap) capable of nitrate reduction using certain electron donors but had yet to be confirmed to express the pathway. In this Example, *Nitrospira inopinata* was confirmed capable of nitrate reduction to nitrite in anoxic conditions when fed ~4 mM formate (FIG. 6A) indicating a broader niche for the comammox organism. Furthermore, several species of *Nitrobacter*, another genus of NOB, have been observed to perform dissimilatory nitrate reduction to ammonia (DNRA) under anoxic conditions and *Nitrospira inopinata* specifically possess the genes for a pentaheme nitrite reductase (NrfAH) to perform DNRA. No consumption of COD was measured in either the co- or counter-diffusing environments, so any heterotrophic metabolisms that occurred in these systems must have received COD from endogenous decay, or $CO_2$ fixation by anammox or other autotrophs present.

Figure 12:
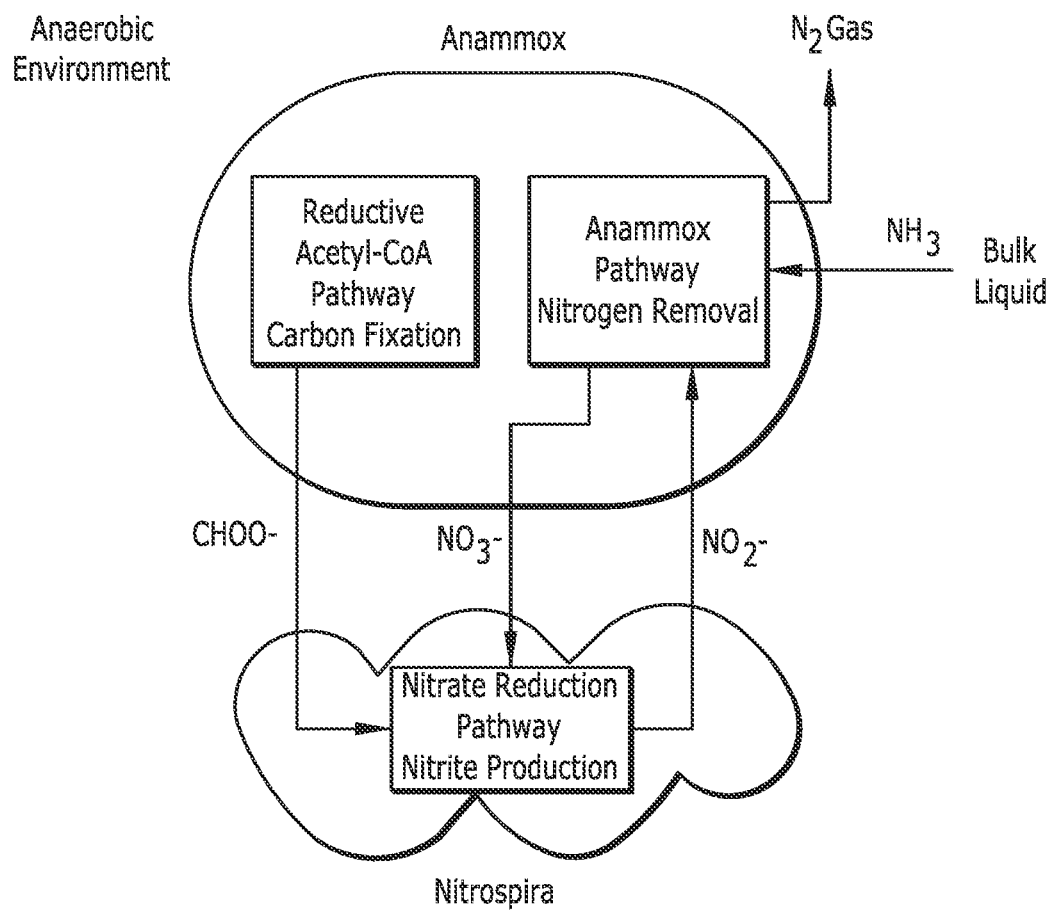
FIG. 12 is a schematic representation of the co-operation between *Nitrospira* and anammox. Anammox produces nitrate ($NO_3^-$) via the anammox nitrogen removal pathway and formate ($CH(O)O^-$) via the carbon fixing reverse acetyl-CoA pathway for *Nitrospira* to anaerobically reduce nitrate to nitrite ($NO_2^-$), which support anammox and allow full nitrogen removal.
Figure 14:
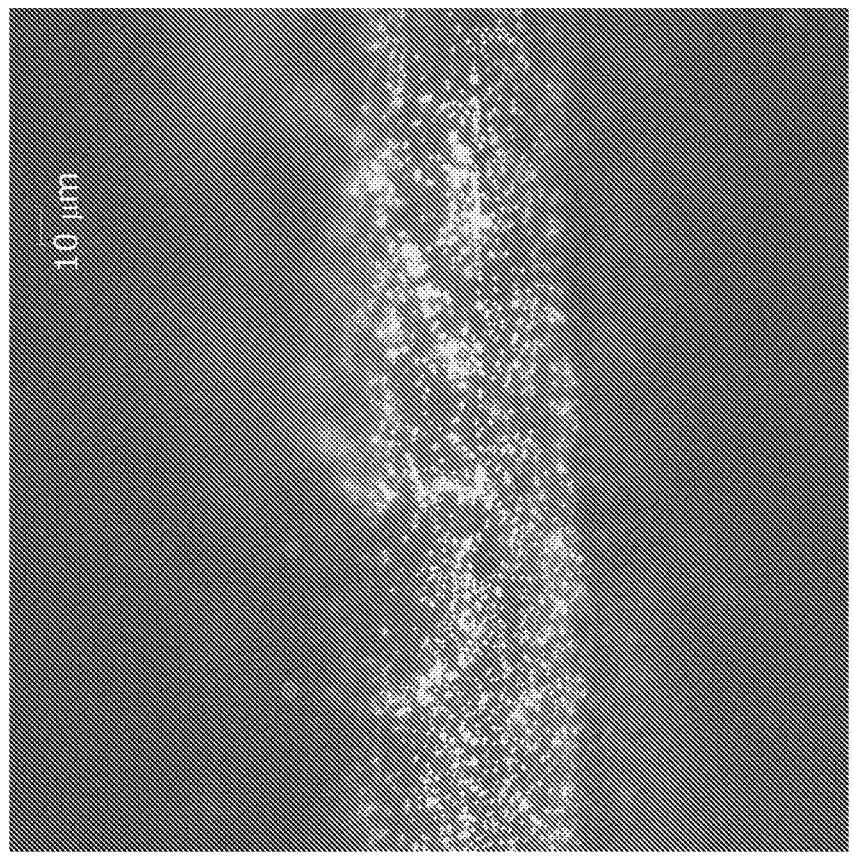
FIG. 14 is a laser scanning confocal micrograph of a microorganism support structure of the present disclosure, having microorganisms attached thereto.
Figure 13:
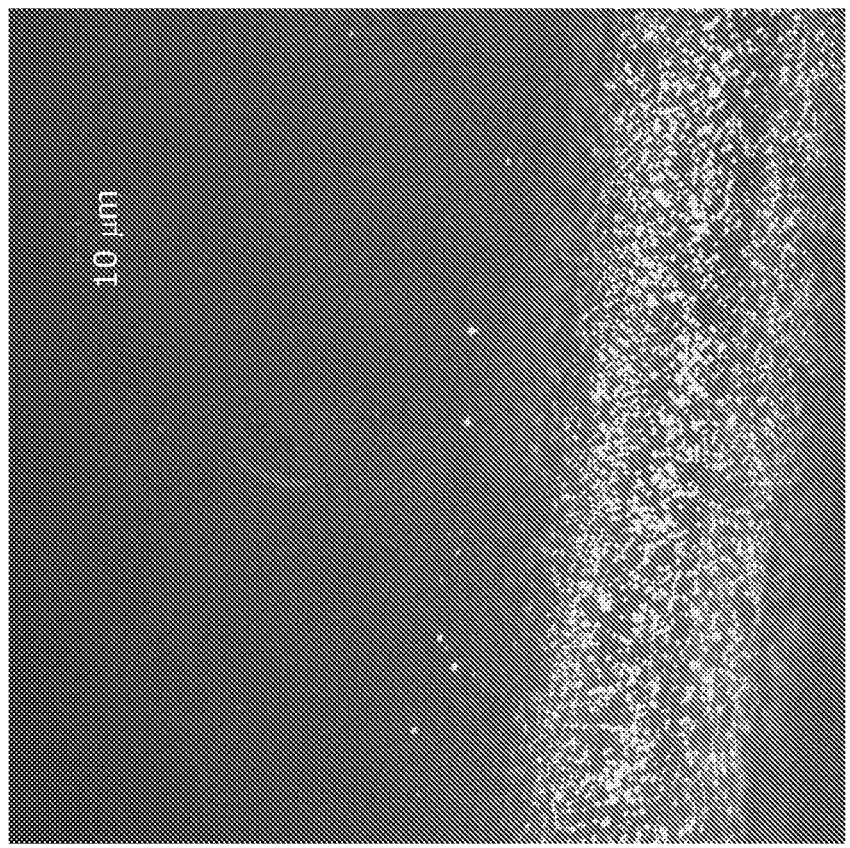
FIG. 13 is a laser scanning confocal micrograph of a microorganism support structure of the present disclosure, having microorganisms attached thereto.
Figure 15A:
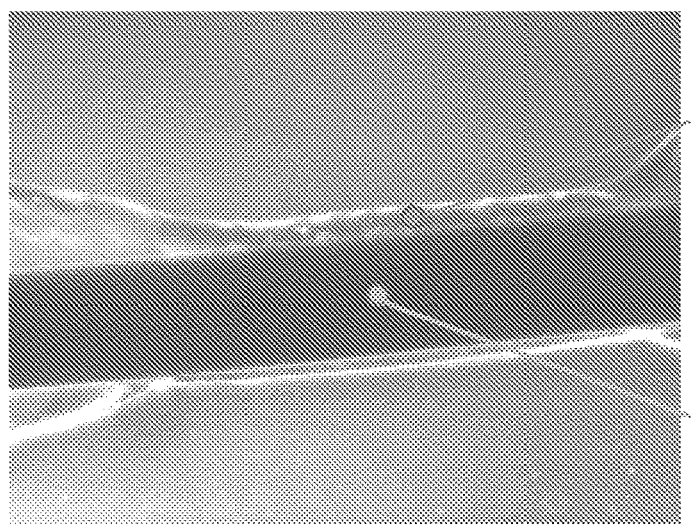
FIGS. 15A-15C are micrographs of a microorganism support structure of the present disclosure, having microorganisms attached thereto.
Figure 15B:
Figure 15C:

Theoretical calculations using the performance data from the counter-diffusing system and previously reported kinetic constants of AOA, anammox, and formate-reducing *Nitrospira* predict that 73% more COD would be required for the denitrification of anammox produced nitrate then could be produced by endogenous decay of autotrophs. The COD deficit leads to the consideration of the possibility of COD supplied via a $CO_2$ fixation pathway. Formate dehydrogenase has been observed to supply formate for DNRA in many organisms. *Ca. Brocadia sinica*, the same genus detected in both counter- and co-diffusing environments, has genes for multiple nitrite/formate transporters and formate dehydrogenase. Formate could be supplied by anammox via the reductive acetyl-CoA pathway, using formate dehydrogenase acting in the reductive direction. Recent metabolic network models built from metatranscriptomic data taken from anammox granular sludge have hypothesized that anammox supplies organic carbon as amines or EPS molecules, along with nitrate, to the heterotrophic populations present in anammox granular sludge. Meanwhile, *Nitrospira* has been reported to use formate and nitrate to form nitrite. This would establish a syntrophic interaction in that anammox supplied both nitrate ($NO_3^-$) and formate ($CHOO^-$) to *Nitrospira* that then supported anammox with nitrite ($NO_2^-$) to perform ammonia ($NH_3$) oxidation to nitrogen gas ($N_2$) (FIG. 12). This co-operation would be a viable hypothesis to explain the absence of nitrate in the effluents of both systems, as there is not enough COD available for typical heterotrophic denitrification.

Urease positive *Nitrospira* can provide ammonia and carbon dioxide to ammonia oxidizers in exchange for nitrite. Here, the observations indicate a more robust co-operation where formate is exchanged as well, including amongst the novel comammox *N. inopinata* (FIG. 12).

Quite strikingly the synthetic counter-diffusion microcosm is comparable to the OMZ in that they both experience counter diffusive gradients, both see AOA-anammox co-operation, have high abundances of NOB (<9% in OMZs, 7-14% in this experiment), they receive little organic carbon, and they accumulate little nitrate, though in marine OMZs the major NOB belongs to the marine *taxa, Nitrospina*. Anammox's competitive edge over any canonical NOB for nitrite is evidenced by the low nitrate effluent concentrations. It is therefore believed that *Nitrospina* (as observed in OMZs) and *Nitrospira* (observed in this study) can perform anaerobic nitrate reduction.

In this Example, a synthetic OMZ-like microcosm replicated partnerships between AOA, NOB and anammox. The microcosm identified two novel nitrite-pathways to supply nitrite to anammox; ammonia oxidation by comammox, and anaerobic reduction of nitrate by *Nitrospira*, including *N. inopinata*. Counter-diffusion was necessary to cultivating a partnership between AOA-anammox, which suggests a pathway forward to implement AOA-anammox into wastewater treatment. These findings indicate that near-complete nitrogen removal at very low oxygen loading rates is possible in both counter and co-diffusing environments which could enable 100% nitrogen removal in the mainstream conditions of wastewater water treatment facilities.

Example 3: Adhesion of Microorganisms to Microorganism Adhesive-Coated Surfaces

The hollow fiber membranes of Examples 1 and 2 were treated in a wet process where the membranes were soaked in a solution open to air containing 1 mM of L-DOPA and 100 mM NaCl at pH of 8.5 for 2-16 hours. An anionic polycatecholamine was deposited on the surface of the membrane fibers. The treated membranes were then rinsed with water and soaked in a polylysine solution for 10-30 minutes to provide a cationic surface. The excess polylysine was rinsed off and the treated membranes are immersed in a suspension of the microbes of interest for 30 minutes. FIGS. 13, 14, and 15A-15C show the microorganisms attached to the surface of the fiber membranes.

By example and without limitation, embodiments are disclosed according to the following enumerated paragraphs:

A1. A microorganism support structure, comprising:
a gas-permeable layer comprising two opposing surfaces;
a microorganism adhesive, coating one surface of the layer; and
a microorganism disposed on the microorganism adhesive-coated surface of the layer.

A2. The microorganism support structure of paragraph A1, wherein the gas-permeable layer is permeable to oxygen, methane, hydrogen, carbon dioxide, carbon monoxide, nitrous oxide, nitric oxide, hydrogen sulfide.

A3. The microorganism support structure of paragraph A1 or paragraph A2, wherein the gas-permeable layer has a gas permeability coefficient of greater than 0.1 Barrer at 25° C.

A4. The microorganism support structure of any one of the preceding paragraphs, wherein the gas-permeable layer comprises a polymeric material, a ceramic material, or a combination thereof.

A5. The microorganism support structure of any one of the preceding paragraphs, wherein the gas-permeable layer is porous, and wherein the pores have a dimension of from 10 nm to 1000 nm.

A6. The microorganism support structure of any one of the preceding paragraphs, wherein the gas-permeable layer is in the form of a hollow tube, a flat sheet, or a spiral-wound membrane.

A7. The microorganism support structure of any one of the preceding paragraphs, wherein the gas-permeable layer has a thickness of from 0.1 mm to 0.5 mm.

A8. The microorganism support structure of any one of the preceding paragraphs, wherein the microorganism adhesive comprises a polypeptide, 3,4-dihydroxyphenyl-l-alanine (L-DOPA), a 3,4-dihydroxyphenyl-l-alanine-containing peptide, polymerized L-DOPA, catecholamines, a peptide including a catecholamine residue, polymerized catechols (e.g., catechols such as urushiol, catechol, catechin, pyrogallol, and similar natural polyphenolic compounds), and derivatives thereof.

A9. The microorganism support structure of paragraph A8, wherein the polypeptide comprises polylysine, polyarginine, polyalanine, polyglutamine, polyglutamic acid, polyaspartic acid, polyhistidine, polyornithine, or any combination thereof.

A10. The microorganism support structure of paragraph A8 or paragraph A9, wherein the polypeptide comprises polylysine.

A11. The microorganism support structure of any one of the preceding paragraphs, wherein the microorganism is attached to the microorganism adhesive-coated surface of the gas-permeable layer.

A12. The microorganism support structure of any one of the preceding paragraphs, wherein the microorganism comprises a single-celled organism.

A13. The microorganism support structure of any one of the preceding paragraphs, wherein the microorganism comprises an archaea, a bacterium, or a combination thereof.

A14. The microorganism support structure of paragraph A13, wherein the archaea, bacterium, or a combination thereof consumes a gas selected from $O_2$, $NH_3$, $CH_4$, $CO_2$, CO, NO, $N_2O$, $H_2$, or a combination thereof to produce a compound selected from $N_2$, methanol, polyhydroxyalcanoates, $CO_2$, $N_2O$, NO, $NH_2OH$, or a combination thereof.

A15. The microorganism support structure of any one of the preceding paragraphs, wherein the microorganism comprises ammonium and/or nitrite oxidizing bacteria or archaea; hydrogen-, carbon compound-, or nitrogen compound-consuming bacteria or archaea; or any combination thereof.

A16. The microorganism support structure of any one of the preceding paragraphs, wherein the microorganism comprises *Nitrospira*, species of ammonia-oxidizing Thaumarchaeota such as *Candidatus nitrosotenuis, Candidatus nitrosoarchaeum, Nitrososphaera viennensis, Nitrosopumilus maritimus, Nitrospira inopinata, Paracoccus denitrificans Methylomonas* sp. LW13, *Gemmatimonas auratiaca, Wollinella succinogenes*, or any combination thereof.

A17. The microorganism support structure of any one of the preceding paragraphs, wherein the microorganism is in the form of a biofilm.

A18. A system, comprising:
  a microorganism support structure comprising a gas-permeable layer comprising two opposing surfaces; a microorganism adhesive, coating one surface of the gas-permeable layer; and a microorganism disposed on the microorganism adhesive-coated surface of the gas-permeable layer; and
  a supply of a gas, wherein the gas is supplied from the surface opposite the surface coated with the microorganism adhesive.

A19. The system of paragraph A18, wherein the gas-permeable layer is in the form of a hollow tube, a flat sheet, or a spiral-wound membrane.

A20. The system of paragraph A18 or paragraph A19, wherein the microorganism comprises a first microorganism, and the gas is a substrate molecule for a first microorganism disposed on the microorganism adhesive-coated surface.

A21. The system of any one of paragraphs A18 to A20, wherein the gas comprises oxygen, $CH_4$, $N_2O$, NO, $H_2$, or a combination thereof.

A22. The system of paragraph A20 or paragraph A21, wherein the microorganism further comprises a second microorganism disposed on the microorganism adhesive-coated surface.

A23. The system of paragraph A22, wherein the second microorganism consumes a product produced by the first microorganism.

A24. The system of any one of paragraphs A18 to A23, further comprising a liquid in contact with the surface on which the microorganism is disposed.

A25. The system of paragraph A25, wherein the liquid supplies a substrate molecule different from the gas for the second microorganism.

A26. The system of paragraph A25, wherein the substrate molecule supplied by the liquid comprises nitrogenous molecules, inorganic carbonaceous molecules, organic carbonaceous molecules, or a phosphate molecule.

A27. The system of any one of paragraphs A24 to A26, wherein the liquid is continuously flowed over the surface on which the microorganism is disposed.

A28. The system of any one of paragraph A24 to A27, wherein the liquid removes a product produced by the first microorganism, the second microorganism, or both the first and second microorganisms.

A29. The system of any one of paragraph A24 to A28, wherein the liquid is wastewater.

A30. The system of paragraph A29, wherein the system converts ammonia in the wastewater to nitrogen at an efficiency of greater than 90% over a period of 3 months or more.

A31. The system of any one of paragraphs A22 to A30, wherein the first and the second microorganisms each independently comprises an archaea or a bacterium.

A32. The system of any one of paragraph A22 to A31, wherein the first and the second microorganisms each independently comprises an ammonium-oxidizing archaea, a complete ammonia oxidizer bacterium, an anaerobic ammonium oxidation bacterium, or any combination thereof.

A33. The system of any one of paragraph A22 to A32, wherein the first microorganism comprises a complete ammonium-oxidizing bacterium or an ammonium-oxidizing archaea, and the second microorganism comprises an anaerobic ammonium oxidation bacterium.

A34. The system of any one of paragraphs A18 to A33, comprising two or more species of bacteria and/or archaea that consume, exchange, or produce a gas selected from $H_2$, $CH_4$, $N_2$, $N_2O$, NO, $O_2$, and any combination thereof.

A35. A method of using a system of any one of paragraphs A18 to A34, comprising continuously supplying the gas from the surface opposite the surface comprising the microorganism, and continuously flowing the liquid over the surface comprising the microorganism.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A microorganism support structure, comprising:
   (a) a gas-permeable layer comprising two opposing surfaces;
   (b) an adhesive, coating one surface of the layer to form an adhesive-coated surface;
   (c) a first microorganism and a second microorganism disposed on the adhesive-coated surface of the layer, wherein the second microorganism is configured to attach to the adhesive-coated surface to form a second microorganism-coated surface of the layer, and the first microorganism is configured to attach to the second microorganism-coated surface such that the second microorganism decreases in population density and number as a function of distance from the gas-permeable layer, and the first microorganism increases in population density and number as a function of distance from the gas-permeable layer, wherein the first microorganism consumes a nitrite produced by the second microorganism.

2. The microorganism support structure of claim 1, wherein the gas-permeable layer is permeable to oxygen, methane, hydrogen, carbon dioxide, carbon monoxide, nitrous oxide, nitric oxide, or hydrogen sulfide.

3. The microorganism support structure of claim 1, wherein the gas-permeable layer has a gas permeability coefficient of greater than 0.1 Barrer at 25° C.

4. The microorganism support structure of claim 1, wherein the gas-permeable layer comprises a polymeric material, a ceramic material, or a combination thereof.

5. The microorganism support structure of claim 1, wherein the gas-permeable layer is porous, and wherein the pores have a dimension of from 10 nm to 1000 nm.

6. The microorganism support structure of claim 1, wherein the gas-permeable layer is in the form of a hollow tube, a flat sheet, or a spiral-wound membrane.

7. The microorganism support structure of claim 1, wherein the adhesive comprises a polypeptide, 3,4-dihydroxyphenyl-l-alanine (L-DOPA), a 3,4-dihydroxyphenyl-l-alanine-containing peptide, polymerized L-DOPA, catecholamines, a peptide including a catecholamine residue, polymerized catechols, and derivatives thereof.

8. The microorganism support structure of claim 7, wherein the polypeptide comprises polylysine, polyarginine, polyalanine, polyglutamine, polyglutamic acid, polyaspartic acid, polyhistidine, polyornithine, or any combination thereof.

9. The microorganism support structure of claim 1, wherein the first microorganism comprises a single-celled organism.

10. The microorganism support structure of claim 1, wherein the first microorganism forms a first layer, the second microorganism forms a second layer, the first layer and second layer together define a total thickness, and wherein the first layer and the second layer together define an overlapping interfacial layer that is from 5% to 95% of the total thickness.

11. A system, comprising:
    (a) the microorganism support structure of claim 1; and
    (b) a supply of a gas, wherein the gas is supplied from the surface opposite the surface coated with the microorganism adhesive.

12. The system of claim 11, wherein the gas comprises oxygen, methane, nitrous oxide, nitric oxide, hydrogen, or a combination thereof.

13. The system of claim 11, wherein the gas is a substrate molecule for the second microorganism.

14. The system of claim 11, further comprising a liquid in contact with the surface on which the microorganism is disposed.

15. The system of claim 14, wherein the liquid supplies a substrate molecule different from the gas for the second microorganism.

16. The system of claim 14, wherein the liquid is continuously flowed over the surface on which the microorganism is disposed.

17. The system of claim 14, wherein the liquid is wastewater.

18. The system of claim 17, wherein the system converts ammonia in the wastewater to nitrogen at an efficiency of greater than 90% over a period of 3 months or more.

19. A method of using a system of claim 14, comprising continuously supplying the gas from the surface opposite the surface comprising the microorganism, and continuously flowing the liquid over the surface comprising the microorganism.

20. The system of claim 11, wherein the system provides a counter-diffusive environment for the first and second microorganisms, such that the gas supplied from the surface opposite the surface on which the microorganisms are disposed decreases in concentration as a function of the distance from the gas-permeable layer; and the substrate molecule supplied by the liquid increases in concentration as a function of the distance from the gas-permeable layer.

* * * * *